(12) United States Patent
Lengauer

(10) Patent No.: US 10,975,029 B2
(45) Date of Patent: Apr. 13, 2021

(54) CRYSTALLINE ERAVACYCLINE BIS-HYDROCHLORIDE

(71) Applicant: Sandoz AG, Basel (CH)

(72) Inventor: Hannes Lengauer, Kundl (AT)

(73) Assignee: Sandoz AG, Basel (CH)

( * ) Notice: Subject to any disclaimer, the term of this patent is extended or adjusted under 35 U.S.C. 154(b) by 141 days.

(21) Appl. No.: 16/071,170

(22) PCT Filed: Jan. 20, 2017

(86) PCT No.: PCT/EP2017/051203
§ 371 (c)(1),
(2) Date: Jul. 19, 2018

(87) PCT Pub. No.: WO2017/125557
PCT Pub. Date: Jul. 27, 2017

(65) Prior Publication Data
US 2020/0199070 A1   Jun. 25, 2020

(30) Foreign Application Priority Data

Jan. 22, 2016  (EP) .................................... 16152468

(51) Int. Cl.
| | |
|---|---|
| *C07D 207/06* | (2006.01) |
| *A61K 9/20* | (2006.01) |
| *A61K 9/48* | (2006.01) |
| *A61K 9/00* | (2006.01) |

(52) U.S. Cl.
CPC .............. *C07D 207/06* (2013.01); *A61K 9/20* (2013.01); *A61K 9/48* (2013.01); *A61K 9/0053* (2013.01); *C07B 2200/13* (2013.01)

(58) Field of Classification Search
CPC .......................... C07B 2200/13; C07D 207/06
See application file for complete search history.

(56) References Cited

U.S. PATENT DOCUMENTS

| | | | | |
|---|---|---|---|---|
| 3,686,168 | A * | 8/1972 | Timreck ............... | C07D 499/00 540/320 |
| 4,432,987 | A * | 2/1984 | Barth .................. | C07D 499/00 514/193 |

(Continued)

FOREIGN PATENT DOCUMENTS

| | | |
|---|---|---|
| WO | 2010017470 A1 | 2/2010 |
| WO | 2012021829 A1 | 2/2012 |

OTHER PUBLICATIONS

Ronn et al. (Org. Process. Res. Dev. 2013, 17, 838-845-provided by applicants in the IDS of Sep. 25, 2018).*

(Continued)

*Primary Examiner* — Valerie Rodriguez-Garcia
(74) *Attorney, Agent, or Firm* — Luedeka Neely Group, P.C.

(57) ABSTRACT

The invention relates to crystalline eravacycline bis-hydrochloride and to a process for its preparation. Furthermore, the invention relates to the use of crystalline eravacycline bis-hydrochloride for the preparation of pharmaceutical compositions. The invention further relates to pharmaceutical compositions comprising an effective amount of crystalline eravacycline bis-hydrochloride. The pharmaceutical compositions of the present invention can be used as medicaments, in particular for treatment and/or prevention of bacterial infections e.g. caused by Gram negative pathogens or Gram positive pathogens, in particular caused by multidrug resistant Gram negative pathogens. The pharmaceutical compositions of the present invention can thus be used as medicaments for e.g. the treatment of complicated intra-abdominal and urinary tract infection.

9 Claims, 7 Drawing Sheets

(56) References Cited

U.S. PATENT DOCUMENTS 5,721,359 A * 2/1998 Dunn ................ C07D 501/00
540/227
7,145,002 B2 * 12/2006 Brands ................ C07D 477/20
540/350

OTHER PUBLICATIONS

Morissette et al. (Advanced Drug Delivery Reviews, 56, (2004) p. 275-300).*
International Search Report and Written Opinion for PCT/EP2017/051203, dated Jun. 27, 2017, 9 pages.
Extended European Search Report for EP App. No. 16152468.1-1462, dated Mar. 15, 2016, 7 pages.
Pecharsky and Zavalij, Fundamentals of Powder Diffraction and Structural Characterization of Minerals, Kluwer Academic Publishers, 2003, p. 3.
Ronn, Magnus, et al., Process R&D of Eravacycline: The First Fully Synthetic Flurorocycline in Clinical Development, Org. Process. Res. Dev., 2013, 17, pp. 838-845.
Xiao, Xiao-Yi, et al., Flurorocyclines. 1.7-Fluoro-9-pyrrolidinoacetamido-6-demethyl-6-deoxytetracycline: A Potent, Broad Spectrum Antibacterial Agent, J. Med. Chem., 2012, 55, pp. 597-605 (English abstract).
OShima, Hiroshi, Crystallization of Polymorphs and Pseudopolymorphs and Its Control, Pharm Stage, Jan. 15, 2007, vol. 6, No. 10, pp. 48-53.

* cited by examiner

CRYSTALLINE ERAVACYCLINE BIS-HYDROCHLORIDE

This application is a Section 371 national phase entry of PCT application PCT/EP2017/051203, filed Jan. 20, 2017. This application also claims the benefit of the earlier filing date of European patent application 16152468.1, filed Jan. 22, 2016.

FIELD OF THE INVENTION

The invention relates to crystalline eravacycline bis-hydrochloride and to a process for its preparation. Furthermore, the invention relates to the use of crystalline eravacycline bis-hydrochloride for the preparation of pharmaceutical compositions. The invention further relates to pharmaceutical compositions comprising an effective amount of crystalline eravacycline bis-hydrochloride. The pharmaceutical compositions of the present invention can be used as medicaments, in particular for the treatment and/or prevention of bacterial infections, e.g. caused by Gram negative pathogens or Gram positive pathogens, in particular caused by multidrug resistant Gram negative pathogens. The pharmaceutical compositions of the present invention can thus be used as medicaments for e.g. the treatment of complicated intra-abdominal and urinary tract infections.

BACKGROUND OF THE INVENTION

Eravacycline is a tetracycline antibiotic chemically designated (4S,4aS,5aR,12aS)-4-(Dimethylamino)-7-fluoro-3,10,12,12a-tetrahydroxy-1,11-dioxo-9-[2-(-pyrrolidin-1-yl) acetamido]-1,4,4a,5,5a,6,11,12a-octahydrotetracene-2-carboxamide and can be represented by the following chemical structure according to formula (I).

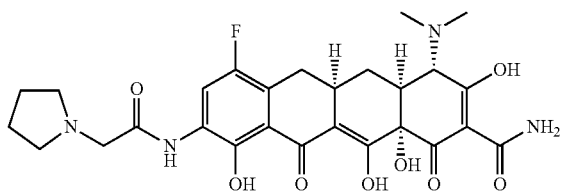

formula (I)

Eravacycline possesses antibacterial activity against Gram negative pathogens and Gram positive pathogens, in particular against multidrug resistant (MDR) Gram negative pathogens and is currently undergoing phase III clinical trials in patients suffering from complicated intra-abdominal infections (cIAI) and urinary tract infections (cUTI).

WO 2010/017470 A1 discloses eravacycline as compound 34. Eravacycline is described to be prepared according to a process, which is described in more detail only for related compounds. The last step of this process involves column chromatography with diluted hydrochloric acid/acetonitrile, followed by freeze drying.

WO 2012/021829 A1 discloses pharmaceutically acceptable acid and base addition salts of eravacycline in general and a general process for preparing the same involving reacting eravacycline free base with the corresponding acids and bases, respectively. On page 15, lines 3 to 6, a lyophilized powder containing an eravacycline salt and mannitol is disclosed.

Xiao et. al. "Fluorocyclines. 1. 7-Fluoro-9-pyrrolidinoacetamido-6-demethyl-6-deoxytetracycline: A Potent, Broad Spectrum Antibacterial Agent" J. Med. Chem. 2012, 55, 597-605 synthesized eravacycline following the procedure for compounds 17e and 17i on page 603. After preparative reverse phase HPLC, compounds 17e and 17i were both obtained as bis-hydrochloride salts in form of yellow solids.

Ronn et al. "Process R&D of Eravacycline: The First Fully Synthetic Fluorocycline in Clinical Development" Org. Process Res. Dev. 2013, 17, 838-845 describe a process yielding eravacycline bis-hydrochloride as the final product. The last step involves precipitation of eravacycline bis-hydrochloride salt by adding ethyl acetate as an antisolvent to a solution of eravacycline bis-hydrochloride in an ethanol/methanol mixture. The authors describe in some detail the difficulties during preparation of the bis-hydrochloride salt of eravacycline. According to Ronn et al. "partial addition of ethyl acetate led to a mixture containing suspended salt and a gummy form of the salt at the bottom of the reactor. At this stage, additional ethanol was added, and the mixture was aged with vigorous stirring until the gummy material also became a suspended solid." In addition, after drying under vacuum the solid contained "higher than acceptable levels of ethanol". "The ethanol was then displaced by water by placing a tray containing the solids obtained in a vacuum oven at reduced pressure ( . . . ) in the presence of an open vessel of water." At the end eravacycline bis-hydrochloride salt containing about 4 to 6% residual moisture was obtained. The authors conclude that there is a need for additional improvements to the procedure along with an isolation step suitable for large scale manufacturing.

It is noteworthy that eravacycline or its salts are nowhere described as being a crystalline solid and that the preparation methods used for the preparation of eravacycline are processes like lyophilization, preparative column chromatography and precipitation, which typically yield amorphous material.

The cumbersome process of Ronn et al. points towards problems in obtaining eravacycline bis-hydrochloride in a suitable solid state, problems with scaleability of the available production process as well as problems with the isolation and drying steps of eravacycline.

In addition, amorphous solids can show low chemical stability, low physical stability, hygroscopicity, poor isolation and powder properties, etc. Such properties are drawbacks for the use as an active pharmaceutical ingredients.

Thus, there is a need in pharmaceutical development for solid forms of an active pharmaceutical ingredient which demonstrate a favorable profile of relevant properties for formulation as a pharmaceutical composition, such as high chemical and physical stability, improved properties upon moisture contact, low(er) hygroscopicity and improved powder properties.

SUMMARY OF THE INVENTION

The present invention solves one or more of the aforementioned problems by providing eravacycline bis-hydrochloride in crystalline form. In particular, the invention provides crystalline eravacycline bis-hydrochloride characterized by having a powder X-ray diffractogram comprising reflections at 2-theta angles of (5.6±0.2)°, (6.0±0.2)°, (7.1±0.2)°, (7.6±0.2°) and (8.6±0.2)°, when measured with Cu-Kalpha$_{1,2}$ radiation having a wavelength of 0.15419 nm, at a temperature in the range of from 20 to 30° C. The invention further relates to a process for the preparation of the crystalline eravacycline bis-hydrochloride of the present invention. The invention further relates to the use of the crystalline eravacycline bis-hydrochloride of the present invention in and/or for the preparation of a pharmaceutical composition. The invention further relates to a pharmaceutical composition comprising an effective amount of crystalline eravacycline bis-hydrochloride.

Definitions

In the context of the present invention the following definitions have the indicated meaning, unless explicitly stated otherwise:

As used herein the term "room temperature" refers to a temperature in the range of from 20 to 30° C.

The term "eravacycline" as used herein refers to (4S,4aS,5aR,12aS)-4-(Dimethylamino)-7-fluoro-3,10,12,12a-tetrahydroxy-1,11-dioxo-9-[2(-pyrrolidin-1-yl)acetamido]-1,4,4a,5,5a,6,11,12a-octahydrotetracene-2-carboxamide according to formula (I) disclosed herein.

The term "eravacycline bis-hydrochloride" as used herein refers to (4S,4aS,5aR,12aS)-4-(Dimethylamino)-7-fluoro-3,10,12,12a-tetrahydroxy-1,11-dioxo-9-[2(-pyrrolidin-1-yl)acetamido]-1,4,4a,5,5a,6,11,12a-octahydrotetracene-2-carboxamide dihydrochloride according to formula (II) disclosed herein.

The term "physical form" as used herein refers to any crystalline and/or amorphous phase of a compound.

As used herein "solvate" refers to a crystalline form of a molecule, atom, and/or ions that further comprises molecules of a solvent or solvents incorporated into the crystal lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. When the solvent is water, the solvate is often referred to as a "hydrate". When the solvent is present in stoichiometric amount, the solvate may be referred to by adding greek numeral prefixes. For example, a hydrate may be referred to as monohydrate, dihydrate, trihydrate, tetrahydrate, etc., depending on the water/eravacycline stoichiometry. The solvent content can be measured, for example, by gas chromatography (GC), 'H-NMR, thermogravimetric analysis (TGA) or in case of water by Karl-Fischer (KF) coulometry.

As used herein "amorphous" refers to a solid form of a compound that is not crystalline. An amorphous compound possesses no long-range order and does not display a definitive X-ray diffraction pattern with reflections.

The term "reflection" with regards to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms and more, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-theta values is in the range of ±0.2° 2-theta, preferably in the range of ±0.1° 2-theta. Thus, a reflection that usually appears at 5.6° 2-theta for example can appear between 5.4° and 5.8° 2-theta, preferably between 5.5 and 5.7° 2-theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

The term "lath" as used herein to describe crystal shape refers to elongated, thin and blade-like crystals.

The term "needle" as used herein to describe crystal shape refers to acicular, thin and highly elongated crystals having similar width and breadth.

The term "column" as used herein to describe crystal shape refers to elongated, prismatic crystals with greater width and thickness than needles.

As used herein, the term "mother liquor" refers to the solution remaining after crystallization of a solid.

The term "antisolvent" as used herein refers to liquids which reduce the solubility of eravacycline bis-hydrochloride in a solvent.

As used herein, the term "water activity" ($a_w$) refers to the ratio of the vapor pressure of water in a liquid (p) to the vapor pressure of pure water ($p_o$) at the same temperature. Water activity can be expressed by the equation $a_w=p/p_o$ and hence ranges from 0.0 aw (no water is present) to 1.0 aw (pure water).

As used herein, the term "substantially pure" with reference to a particular physical form means that the physical form includes less than 10%, preferably less than 5%, more preferably less than 3%, most preferably less than 1% by weight of any other physical forms of the compound. Crystalline eravacycline bis-hydrochloride may be referred to herein as being characterized by graphical data "as shown in" a Figure. Such data include, for example, powder X-ray diffractograms (PXRD), differential scanning calorimetry (DSC) thermograms and thermogravimetric analysis (TGA). The person skilled in the art understands that factors such as variations in instrument type, response and variations in sample directionality, sample concentration, sample purity, sample history and sample preparation may lead to variations for such data when presented in graphical form, for example variations relating to the exact peak positions and intensities. However, a comparison of the graphical data in the Figures herein with the graphical data generated for an unknown physical form and the confirmation that two sets of graphical data relate to the same crystal form is well within the knowledge of a person skilled in the art.

"Reduced pressure" as used herein means a pressure in the range of from 10 mbar to 900 mbar.

"Relative humidity" as used herein refers to the ratio of the partial pressure of water vapor to the equilibrium vapor pressure of water at the same temperature. Relative humidity depends on temperature and the pressure of the system of interest. Unless otherwise specified, the temperature is 25° C. and the pressure is 1013 mbar.

A "stabilizer" as used herein is a pharmaceutical excipient which helps to stabilize eravacycline during lyophilization and during storage of the lyophilisate. A stabilizer is an organic compound capable of reducing epimer formation in a lyophilisate wherein eravacycline and said stabilizer are the only organic compounds and wherein the lyophilisate is prepared at a pH of 4.8, when compared to a lyophilisate wherein eravacycline is the only organic compound and the lyophilisate is prepared at the same pH.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

DETAILED DESCRIPTION OF THE INVENTION

Figure 1:
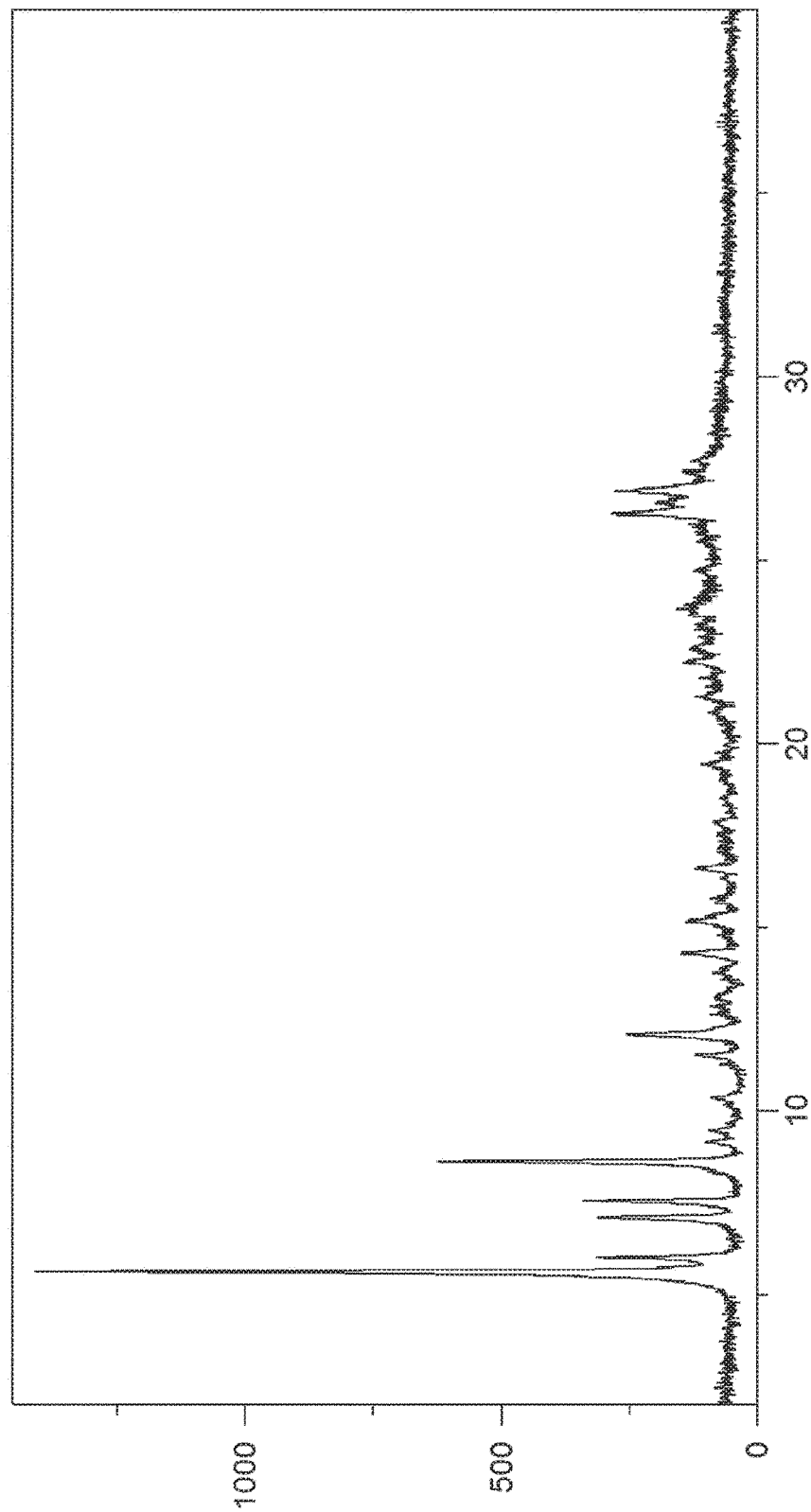
FIG. 1: illustrates a representative powder X-ray diffractogram of crystalline eravacycline bis-hydrochloride. The x-axis shows the scattering angle in ° 2-theta, the y-axis shows the intensity of the scattered X-ray beam in counts of detected photons. The powder X-ray diffractogram was recorded at room temperature and at 30% relative humidity.

The present invention provides eravacycline bis-hydrochloride in crystalline form.

Crystallizing eravacycline bis-hydrochloride was not straightforward. Many attempts to obtain eravacycline bis-hydrochloride crystals were not successful until first seed crystals were obtained by serendipity under very specific conditions. Only with these seed crystals in hands for the first time, the inventors of the present invention were able to develop a scaleable process for the preparation of crystalline eravacycline bis-hydrochloride which does not suffer from the drawback of going through gummy material as an intermediate. In addition, crystalline eravacycline bis-hydrochloride of the present invention shows excellent isolation properties such as good filtration properties, and can be easily dried after isolation.

Moreover, crystalline eravacycline bis-hydrochloride of the present invention shows improved chemical and physical stability over a broad humidity range compared to amorphous eravacycline bis-hydrochloride. One concern with amorphous eravacycline bis-hydrochloride is for example its tendency for deliquescence. It was found that amorphous eravacycline bis-hydrochloride liquefies at a relative humidity of 85%, when measured at $25.0\pm0.1°$ C. In contrast, the crystalline eravacycline bis-hydrochloride of the present invention liquefies at a higher relative humidity of 95% when measured at $25.0\pm0.1°$ C. This favors the crystalline eravacycline bis-hydrochloride of the present invention to be used for storage and shipping.

Another concern with amorphous eravacycline is its property to take up water from the surrounding atmosphere faster than releasing it again. Due to this special property of amorphous eravacycline bis-hydrochloride, its water content not only depends on the relative humidity of the surrounding atmosphere but also on the previous history of the sample (e.g. previous drying and storage conditions). This renders the formulation of a uniform drug product extremely challenging, since controlling the relative humidity of the atmosphere may not be sufficient to adjust a particular water content.

In contrast, crystalline eravacycline bis-hydrochloride of the present invention takes up and releases water equally fast. Thus, its water content can be adjusted by simply equilibrating the sample at a certain relative humidity.

On top of that, crystalline eravacycline bis-hydrochloride is less hygroscopic compared to amorphous eravacycline bis-hydrochloride.

Crystalline eravacycline bis-hydrochloride thus has excellent physicochemical properties, which enable the crystalline eravacycline bis-hydrochloride of the present invention to be used in and/or for the preparation of a uniform pharmaceutical composition, in particular a pharmaceutical composition comprising an effective amount of crystalline eravacycline bis-hydrochloride for oral administration or a pharmaceutical composition comprising eravacycline, for example an eravacycline hydrochloride salt, intended for parenteral use. Crystalline eravacycline bis-hydrochloride further ensures that pharmaceutical compositions comprising it have a continuous high bioavailability throughout shelf-life. Furthermore, the crystalline eravacycline bis-hydrochloride of the present invention is a solid form of eravacycline, which is more convenient to handle during pharmaceutical processes for example which is easier to isolate in the final step of the chemical synthesis and easier to handle during formulation of a drug product.

In one aspect, the present invention relates to crystalline eravacycline bis-hydrochloride.

Preferably, the present invention relates to crystalline eravacycline bis-hydrochloride of formula (II)

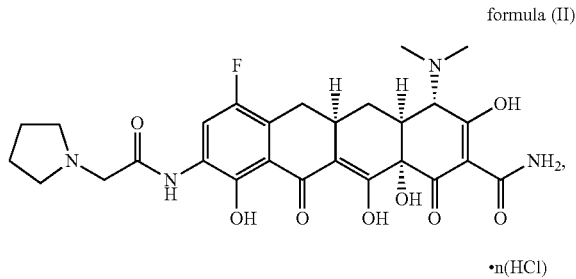 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

formula (II)

•n(HCl)

wherein n is 2, preferably wherein n is in the range of from 1.8 to 2.2, more preferably from 1.9 to 2.1, and most preferably wherein n is 2.0.

In a further embodiment, the invention relates to crystalline eravacycline bis-hydrochloride of formula (II)

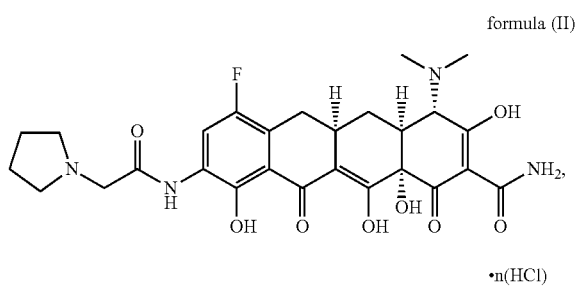 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

formula (II)

•n(HCl)

wherein n is 2, preferably wherein n is in the range of from 1.8 to 2.2, more preferably from 1.9 to 2.1, and most preferably wherein n is 2.0, and wherein the crystalline eravacycline bis-hydrochloride is preferably a solvate or a hydrate, more preferably a non-stoichiometric hydrate.

The present invention also relates to crystalline eravacycline bis-hydrochloride of formula (III)

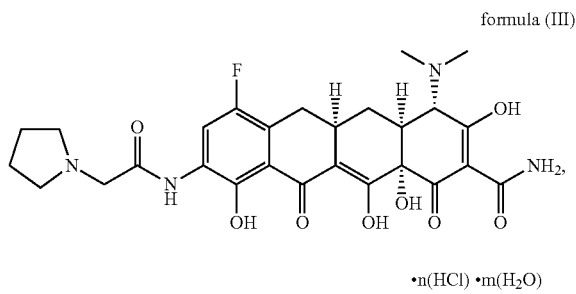 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

formula (III)

•n(HCl) •m(H₂O)

wherein n is 2, preferably wherein n is in the range of from 1.8 to 2.2, more preferably from 1.9 to 2.1, and most preferably wherein n is 2.0,
and wherein m is in the range of from about 0.0 to 9.0.

In a preferred embodiment, crystalline eravacycline bis-hydrochloride of the invention can be characterized by having a powder X-ray diffractogram comprising reflections at 2-Theta angles selected from:
(a) (5.6±0.2)° and (8.6±0.2)°; or
(b) (5.6±0.2)°, (6.0±0.2)° and (8.6±0.2)°; or
(c) (5.6±0.2)°, (6.0±0.2)°, (7.1±0.2)° and (8.6±0.2)°; or
(d) (5.6±0.2)°, (6.0±0.2)°, (7.1±0.2)°, (7.6±0.2)° and (8.6±0.2)°; or
(e) (5.6±0.2)°, (6.0±0.2)°, (7.1±0.2)°, (7.6±0.2)°, (8.6±0.2)° and (12.1±0.2°); or
(f) (5.6±0.2)°, (6.0±0.2)°, (7.1±0.2)°, (7.6±0.2)°, (8.6±0.2)°, (12.1±0.2)° and (26.3±0.2°); or
(g) (5.6±0.2)°, (6.0±0.2)°, (7.1±0.2)°, (7.6±0.2)°, (8.6±0.2)°, (12.1±0.2)°, (26.3±0.2°) and (26.9±0.2°); or
(h) (5.6±0.2)°, (6.0±0.2)°, (7.1±0.2)°, (7.6±0.2)°, (8.6±0.2)°, (11.5±0.2)°, (12.1±0.2)°, (26.3±0.2°) and (26.9±0.2°); or
(i) (5.6±0.2)°, (6.0±0.2)°, (7.1±0.2)°, (7.6±0.2)°, (8.6±0.2)°, (11.5±0.2)°, (12.1±0.2)°, (14.3±0.2)°, (26.3±0.2°) and (26.9±0.2°); or
(j) (5.6±0.2)°, (6.0±0.2)°, (7.1±0.2)°, (7.6±0.2)°, (8.6±0.2)°, (11.5±0.2)°, (12.1±0.2)°, (14.3±0.2)°, (15.2±0.2)°, (26.3±0.2°) and (26.9±0.2°);
(k) (6.0±0.2)°, (7.1±0.2)°, (7.6±0.2)°, (8.6±0.2)°, (12.1±0.2)°, (26.3±0.2°) and (26.9±0.2°);
(l) (6.0±0.2)°, (7.1±0.2)°, (7.6±0.2)°, (8.6±0.2)°, (12.1±0.2)°, and (26.3±0.2°);
(m) (6.0±0.2)°, (7.1±0.2)°, (7.6±0.2)°, (8.6±0.2)°, and (12.1±0.2)°; (n) (6.0±0.2)°, (7.1±0.2)°, (7.6±0.2)°, and (8.6±0.2)°;
(o) (7.1±0.2)°, (7.6±0.2)°, (8.6±0.2)°, (12.1±0.2)°, (26.3±0.2°) and (26.9±0.2°);
(p) (7.1±0.2)°, (7.6±0.2)°, (8.6±0.2)°, (12.1±0.2)°, and (26.3±0.2°);
(q) (7.1±0.2)°, (7.6±0.2)°, (8.6±0.2)°, and (12.1±0.2°);
(r) (7.1±0.2)°, (7.6±0.2)° and (8.6±0.2°);
when measured with Cu-Kalpha$_{1,2}$ radiation at a wavelength of 0.15419 nm, room temperature, and preferably when measured at 30% relative humidity.

Alternatively, crystalline eravacycline bis-hydrochloride of the invention can be characterized by having a powder X-ray diffractogram which is essentially the same as displayed in FIG. 1 of the present invention, when measured with Cu-Kalpha$_{1,2}$ radiation at a wavelength of 0.15419 nm and room temperature, preferably when measured at 30% relative humidity.

In a preferred embodiment, the crystalline eravacycline bis-hydrochloride of the present invention comprises at most 20 weight %, preferably at most 10 weight %, more preferably at most 5 weight %, even more preferably at most 2 weight % and most preferably at most 1 weight %, of any other physical form of eravacycline bis-hydrochloride, based on the weight of the crystalline eravacycline bis-hydrochloride of the present invention. Most preferably, the any other physical form of eravacycline bis-hydrochloride is amorphous eravacycline bis-hydrochloride.

Alternatively or additionally, the present invention relates to crystalline eravacycline bis-hydrochloride characterized by showing a mass loss in the range of from 10.0 to 10.5 weight %, preferably from 10.2 to 10.4 weight %, based on the weight of the crystalline eravacycline bis-hydrochloride, when equilibrated at a relative humidity in the range of from about 25 to 30% and 25° C. and then analyzed by thermogravimetric analysis at a temperature in the range of from 25 to 170° C. and a heating rate of 10 K/min.

Alternatively or additionally, the present invention relates to crystalline eravacycline bis-hydrochloride characterized by having a water content in the range of from about 10.0 to 10.5 weight %, preferably from about 10.2 to 10.4 weight %, based on the weight of the crystalline eravacycline bis-hydrochloride, said crystalline eravacycline bis-hydrochloride being equilibrated at a relative humidity in the range of from about 25 to 30% and room temperature, as determined by Karl-Fischer-Coulometry.

The present invention also relates to crystalline eravacycline bis-hydrochloride characterized by a water content in the range of from about 0.0 to about 20.1% when equilibrated at a relative humidity in the range of from about 0 to 90% and 25.0±0.1° C., as determined by Karl-Fischer-Coulometry.

Preferably, the crystalline eravacycline bis-hydrochloride of the present invention is a non-stoichiometric hydrate.

In a further embodiment, the present invention relates to crystalline eravacycline bis-hydrochloride characterized by showing a differential scanning calorimetry curve comprising an endothermic peak in the temperature range of from about 35 to 170° C., said peak preferably being a broad peak extending over said temperature range, when measured at a heating rate of 10 K/min.

The crystalline eravacycline bis-hydrochloride of the present invention can further be characterized by comprising crystals having needle, lath and/or column shape.

In a preferred embodiment, the crystalline eravacycline bis-hydrochloride of the present invention comprises needle, lath and/or column shaped crystals, characterized by having a length of not more than 30 µm, preferably not more than 20 µm for example not more than 10 µm.

The invention also relates to a composition comprising at least 90 weight % of crystalline eravacycline bis-hydrochloride of the present invention, based on the total weight of the composition. Preferably, the composition comprises less than 5 weight % amorphous eravacycline bis-hydrochloride, such as less than 2 weight % amorphous eravacycline bis-hydrochloride based on the total weight of the composition.

The invention also relates to a composition comprising at least 95 weight % of crystalline eravacycline bis-hydrochloride of the present invention, based on the total weight of the composition. Preferably, the composition comprises less than 4 weight % amorphous eravacycline bis-hydrochloride, such as less than 2 weight % amorphous eravacycline bis-hydrochloride, based on the total weight of the composition.

In a further aspect, the invention relates to a process for the preparation of crystalline eravacycline bis-hydrochloride of the present invention comprising:
(i) providing an aqueous solution of eravacycline bis-hydrochloride and at least one organic antisolvent, wherein the aqueous solution is characterized by a water activity of at least 0.1, and wherein the organic antisolvent is selected from the group of ketones and ethers;
(ii) adding eravacycline bis-hydrochloride seed crystals of the present invention to the solution provided in step (i) and allowing dissolved eravacycline bis-hydrochloride to crystallize;
(iii) optionally adding further antisolvent to the suspension obtained in step (ii); (iv) optionally separating at least a part of the crystalline eravacycline bis-hydrochloride obtained in (ii) or (iii) from its mother liquor;
(v) optionally washing the isolated crystals obtained in step (iv); and
(vi) optionally drying the eravacycline bis-hydrochloride crystals obtained in any one of the steps (ii) to (v);

The aqueous solution of step (i) comprising eravacycline bis-hydrochloride may be prepared either by dissolving amorphous eravacycline bis-hydrochloride in the aqueous solvent or by reacting eravacycline free base with hydrochloric acid in the presence of the aqueous solvent in order to obtain eravacycline bis-hydrochloride in situ. In the latter case the free base is reacted with at least 1.7 mol equivalents, preferably at least 2.0 mol equivalents, for example at least 2.2 mol equivalents of hydrochloric acid. Preferably, aqueous hydrochloric acid is used for the reaction. The solution may be prepared at room temperature or at elevated temperature, most preferably at room temperature.

Amorphous eravacycline free base and amorphous eravacycline bis-hydrochloride, which may be used as starting material, can for example both be prepared according to the procedures disclosed in Ronn et al. "Process R&D of Eravacycline: The First Fully Synthetic Fluorocycline in Clinical Development" Org. Process Res. Dev. 2013, 17, 838-845 (compound 7 corresponds to eravacycline free base and compound 7.2HCl corresponds to eravacycline bis-hydrochloride).

The final eravacycline bis-hydrochloride concentration of the aqueous solution of step (i) preferably is in the range of from about 5 to 50 g/L, more preferably from about 5 to 25 g/L and most preferably from about 5 to 15 g/L.

The at least one organic antisolvent may be selected from the group of ketones and ethers. Specific examples for suitable antisolvents which may advantageously be used are acetone and 1,2-dimethoxyethane, with acetone being preferred.

Subsequently, seed crystals of eravacycline bis-hydrochloride are added to the solution in order to initiate crystallization. Seed crystals may be prepared according to the procedure described in example 2 herein.

The production of first seed crystals was very cumbersome. Many different other processes to prepare seed crystals of eravacycline bis-hydrochloride had failed before the process of example 2 yielded first crystalline material. With crystalline eravacycline bis-hydrochloride in hands, seed crystals can also be prepared according to the procedure disclosed in example 1 herein.

The amount of seed crystals applied preferably is in the range of from 1 to 10 weight %, more preferably from 2 to 5 weight %, based on the amount of eravacycline bis-hydrochloride present in the aqueous solution provided in step (i).

After seeding, the mixture is preferably subjected to a stir-out period. The stir-out period encompasses any kind of movement of the solid material suspended in the solvent caused by, but not limited to e.g. agitation, stirring, mixing, shaking, vibration, sonication, wet milling and the like and is preferably performed at room temperature. Usually, the suspension is preferably stirred for a period in the range of from 1 to 48 hours, more preferably from 2 to 24 hours and most preferably from 3 to 12 hours.

Optionally, in a subsequent step at least one additional antisolvent may be added to the suspension in order to increase the yield of crystalline eravacycline bis-hydrochloride. The at least one additional antisolvent is preferably the same as already used in the initial solution provided in step (i).

Optionally, in a subsequent step, at least a part of the crystalline eravacycline bis-hydrochloride is separated from its mother liquor. Preferably, the eravacycline bis-hydrochloride crystals are separated from their mother liquor by any conventional method such as filtration, centrifugation, solvent evaporation or decantation, more preferably by filtration or centrifugation and most preferably by filtration.

Optionally, in a further step the isolated crystals are washed with a suitable solvent. Suitable solvents comprise but are not limited to acetone and 1,2-dimethoxyethane.

The obtained crystalline eravacycline bis-hydrochloride crystals may optionally be dried. Drying may be performed at a temperature of about 40° C. or less, preferably of about 30° C. or less and most preferably drying is performed at room temperature. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 20 mbar or less.

No gummy residue is observed during the above described process. This is advantageous because gummy material tends to stick on the reactor wall and stirrer, which can lead to yield loss and subsequent cumbersome cleaning work of the equipment. According to Ronn et. al. the gummy residue observed in their procedure could only be removed by aging with vigorous stirring, which on the one hand is time-consuming and on the other hand strongly impacts particle shape and size due to the mechanical stress and therefore negatively influences the isolation properties of the material.

Figure 4:
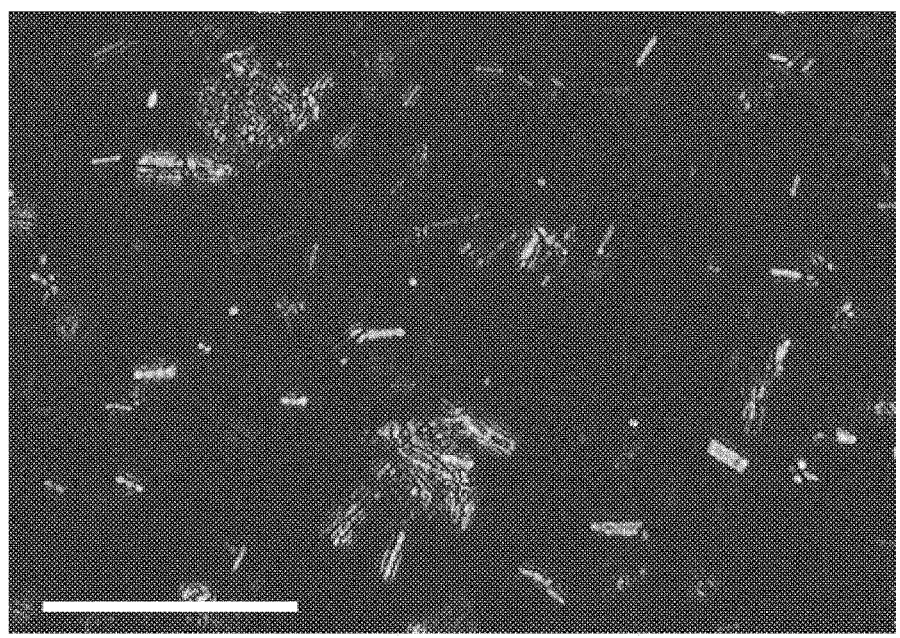
FIG. 4: shows a photomicrographic image of eravacycline bis-hydrochloride crystals taken with a polarized light microscope (scale bar=50 micrometer).

In contrast, the crystalline eravacycline bis-hydrochloride of the present invention shows excellent isolation properties, such as good filtration properties, and can be dried easily after isolation. This is mainly due to the fact that the bulk of the material consists of well-defined lath-shaped crystals (see also FIG. 4 herein). The avoidance of gummy material throughout the process is advantageous as it saves time, effort and leads to material with improved purity and/or improved powder properties.

Crystalline eravacycline bis-hydrochloride exhibits physicochemical properties which favor this physical form to be used for and/or in the preparation of pharmaceutical compositions over the material described in Ronn et. al. Besides improved chemical stability (see comparative example 2 herein), crystalline eravacycline bis-hydrochloride of the present invention is also physically more stable. For example, the crystalline eravacycline bis-hydrochloride of the present invention does not liquefy when subjected to a relative humidity in the range of from about 0 to 90% at 25.0±0.1° C., but remains in the solid state. In contrast, amorphous eravacycline bis-hydrochloride showed deliquescence at 85% relative humidity, rendering this physical form more difficult to handle and requiring precautionary measures against moisture.

The present inventors have identified an additional concern with amorphous eravacycline bis-hydrochloride. Amorphous eravacycline bis-hydrochloride takes up water from the surrounding atmosphere faster than releasing it again. Due to this special property of amorphous eravacycline bis-hydrochloride, its water content not only depends on the relative humidity of the surrounding atmosphere but also on the previous history of the sample (e.g. previous drying and storage conditions). This renders the formulation of a uniform drug product challenging, since controlling the relative humidity of the atmosphere may not be sufficient to adjust a particular water content. As can be seen from FIG. 7 the gravimetric moisture sorption and desorption curve of amorphous eravacycline bis-hydrochloride show a significant hysteresis. At 40% relative humidity for example, the water content may vary from about 8.9 weight % in the sorption curve to 14.3% in the desorption curve.

In contrast, crystalline eravacycline bis-hydrochloride of the present invention takes up and releases water equally fast. Thus, its water content can be adjusted by simply equilibrating the sample at a certain relative humidity. As can be seen from FIG. 6 the gravimetric moisture sorption and desorption curve of crystalline eravacycline bis-hydrochloride show no significant hysteresis. At 40% relative humidity for example, a water content of about 13 weight % was measured during the sorption and the desorption cycle. This unique property of crystalline eravacycline bis-hydrochloride allows for a straightforward formulation of a uniform drug product.

On top of that, crystalline eravacycline bis-hydrochloride is less hygroscopic compared to amorphous eravacycline bis-hydrochloride. Amorphous eravacycline bis-hydrochloride shows a mass increase of about 26.1 weight % during the sorption cycle from 0 to 80% RH compared to a weight gain of 17.7 weight % for crystalline eravacycline bis-hydrochloride in the same range. Overall, crystalline eravacycline bis-hydrochloride of the present invention shows a combination of physicochemical properties which are favorable, for example, for storage, for shipping, for use as an intermediate in the preparation of a pharmaceutical composition, or also for use as the active pharmaceutical ingredient in a pharmaceutical composition.

Therefore in a further aspect the present invention relates to a pharmaceutical composition comprising an effective amount of the crystalline eravacycline bis-hydrochloride of the invention, and one or more pharmaceutically acceptable excipient(s). The pharmaceutical composition is preferably an oral solid dosage form, such as a tablet or a capsule.

The pharmaceutical composition may be formulated with one or more pharmaceutically acceptable excipients and optionally other active pharmaceutical ingredients. Pharmaceutically acceptable excipients relate to substances known for example from the European Pharmacopeia (Ph. Eur.). Pharmaceutically acceptable excipients which may be used are for example selected from the group of carriers, fillers, diluents, lubricants, sweeteners, stabilizing agents, solubilizing agents, antioxidants and preservatives, flavouring agents, binders, colorants, osmotic agents, buffers, surfactants, disintegrants, granulating agents, coating materials and combinations thereof.

The pharmaceutical composition of the present invention can be prepared by wet or dry processing methods. In certain embodiments the pharmaceutical compositions are prepared by wet processing methods, such as, but not limited to, wet granulation methods. Suitable wet granulation methods comprise high-shear granulation or fluid-bed granulation. In another embodiment the pharmaceutical compositions are prepared by dry processing methods, such as, but not limited to, direct compression or dry granulation methods. An example of dry granulation is roller compaction. The pharmaceutical compositions obtained by dry or wet processing methods may be compressed into tablets, encapsulated or metered into sachets.

In a preferred embodiment, the present invention relates to a pharmaceutical composition as described above, wherein crystalline eravacycline bis-hydrochloride is present in a dose of 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 350 mg, 400 mg, 450 mg or 500 mg, calculated as eravacycline free base.

In a further preferred embodiment, the present invention relates to a pharmaceutical composition as described above, wherein the pharmaceutical composition is to be administered once daily or once every second day.

Preferably, the present invention relates to a pharmaceutical composition as described above, wherein the pharmaceutical composition is to be administered without food.

In yet another aspect, the invention relates to the use of crystalline eravacycline bis-hydrochloride of the present invention for the preparation of a pharmaceutical composition comprising eravacycline. Preferably, the crystalline eravacycline bis-hydrochloride of the present invention can be used in the process for the preparation of a pharmaceutical composition comprising eravacycline, for example eravacycline hydrochloride, intended for parenteral use. Preferably, the pharmaceutical composition intended for parenteral use of the present invention is a powder for solution for infusion and most preferably a lyophilized powder for solution for infusion. The skilled person will appreciate that the lyophilized powder for solution for infusion in general will not comprise the crystalline eravacycline bis-hydrochloride of the present invention itself, but that the crystalline eravacycline bis-hydrochloride of the present invention is used as an intermediate before or as a starting material for the process for the preparation of a lyophilized powder for solution for infusion comprising eravacycline.

Thus, in a further aspect, the present invention relates to a process for the preparation of a pharmaceutical composition comprising eravacycline intended for parenteral use comprising the steps of:
(i) providing crystalline eravacycline bis-hydrochloride of the present invention and optionally at least one stabilizer selected from the group of sugars and/or sugar alcohols;
(ii) dissolving or suspending crystalline eravacycline bis-hydrochloride and said optionally at least one stabilizer provided in step (i) in a solvent comprising water;
(iii) adjusting the pH of the solution or suspension obtained in step (ii) by adding at least one acid or base;
(iv) optionally filtering the solution or suspension obtained in step (iii) and (v) lyophilizing the solution or suspension obtained in any one of steps (ii) to (iv) to give a pharmaceutical composition comprising eravacycline.

The order of steps (i), (ii), (iii), (iv), and (v) above can be sequential, but variations of this process are well within the scope of the skilled person. For example, in a variation of steps (i) and (ii) eravacycline bis-hydrochloride may be dissolved in a solution comprising the dissolved stabilizer. Alternatively, the at least one stabilizer may be dissolved in a solution comprising eravacycline bis-hydrochloride.

An example of an acid for pH adjustment in step (iii) of the above described process is hydrochloric acid, preferably in form of an aqueous solution. An example for a base for pH adjustment in step (iii) is sodium hydroxide, preferably in form of an aqueous solution.

In one aspect, the pH environment is from 3.0 to 7.0, such as pH values from about 4.0 to about 5.0, or from about 4.2 to about 4.8.

The stabilizer is preferably a carbohydrate, such as a sugar. Preferred sugars include mono- and disaccharides, more preferably monosaccharides, such as mannose and glucose, and disaccharides, such as lactose and sucrose. Stabilizing sugars may be provided as different enantiomers, such as D-glucose and L-glucose, and/or as different solid forms. For example, lactose includes the various solid forms of lactose, e.g. anhydrous lactose, lactose monohydrate or another hydrated or solvated form of lactose.

An example of a sugar, which can be added as stabilizer in step (i) of the above described process, is lactose, preferably lactose monohydrate. An example for a sugar alcohol, which can be added as stabilizer in step (i) of the above described process, is mannitol.

Preferred molar ratios of eravacycline to stabilizer, for example lactose, in the lyophilized powder or cake are from 1.0 (eravacycline):0.3 (stabilizer) to 1:4. The molar ratio of eravacycline to stabilizer may also be in the range of from 1.0:1.0 to 1.0:3.0.

In one example of a process for the preparation of a pharmaceutical composition of the invention, crystalline eravacycline dihydrochloride is dissolved in water to form a solution. The pH of the solution is subsequently lowered by addition of an acid or buffer to obtain a pH from about 4.0 to about 5.0. A stabilizer, for example a carbohydrate such as lactose, is then dissolved in the solution and the solution is filtered, e.g. sterile filtered, and lyophilized to dryness to form a lyophilized powder or cake.

In another example of a process for the preparation of a pharmaceutical composition of the invention, lactose, for example 106 mg lactose monohydrate, is dissolved in water and cooled to 2-8° C. with nitrogen purging. Crystalline eravacycline bis-hydrochloride according to the present invention is dissolved in the cooled lactose solution to form a solution. The pH of the solution is subsequently lowered by addition of hydrochloric acid to obtain a pH from 4.0 to 5.5, for example pH 4.9. The pH-adjusted solution is then sterile filtered. About 3.5 mL solution (comprising 53 mg eravacycline bis-hydrochloride) per vial are then filled into lyophilization vials. Lyophilization is then carried out at a temperature below −40° C. until the water content is low, for example at most 1% w/w. Vials are filled with nitrogen to about 500 mbar and then closed with a pharmaceutically acceptable stopper which contains essentially no leachable zinc, and then crimped with a crimping cap.

In a further aspect the present invention relates to a pharmaceutical composition obtainable or obtained by, and preferably prepared according to, the above defined process.

The pharmaceutical compositions of the invention also include solutions prepared from the lyophilisate by e.g. reconstitution with physiological saline. The pharmaceutical composition intended for parenteral use of the present invention is preferably administered by intravenous infusion after reconstitution with sodium chloride, for example 9 mg/mL (0.9%), solution for injection, dextrose, for example 50 mg/mL (5%), solution for injection or Lactated Ringer's solution for injection.

The invention further relates to the pharmaceutical composition of the present invention for use as a medicament, in particular for use in the treatment and/or prevention of bacterial infections, wherein the bacterial infections are caused by Gram negative or Gram positive bacteria, in particular by multidrug resistant Gram negative bacteria. The pharmaceutical composition of the present invention is for example suitable for the treatment and/or prevention of complicated intraabdominal and complicated urinary tract infections.

Embodiment Section

Aspects, advantageous features and preferred embodiments of the present invention are summarized in the following items:
1) Crystalline eravacycline bis-hydrochloride.
2) Crystalline eravacycline bis-hydrochloride of formula (II)

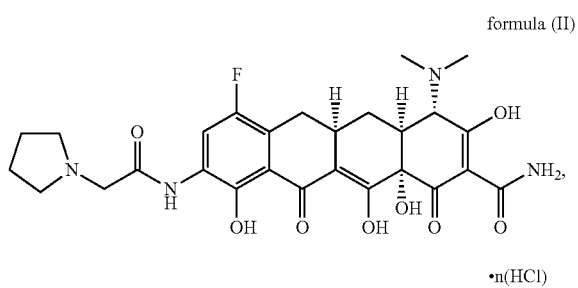 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

formula (II)

•n(HCl)

wherein n is in the range of from 1.8 to 2.2.
3) Crystalline eravacycline bis-hydrochloride of formula (II)

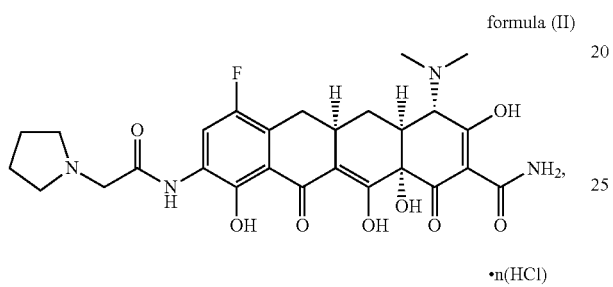

formula (II)

•n(HCl)

wherein n is in the range of from 1.9 to 2.1.
4) Crystalline eravacycline bis-hydrochloride of formula (II)

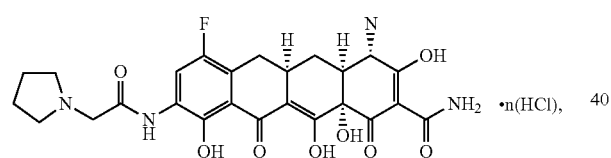

formula (II) •n(HCl), wherein n is 2.0.
5) Crystalline eravacycline bis-hydrochloride according to any one of items 1 to 4, wherein the crystalline eravacycline bis-hydrochloride is a solvate.
6) Crystalline eravacycline bis-hydrochloride according to any one of items 1 to 4, wherein the crystalline eravacycline bis-hydrochloride is a hydrate.
7) Crystalline eravacycline bis-hydrochloride of formula (III)

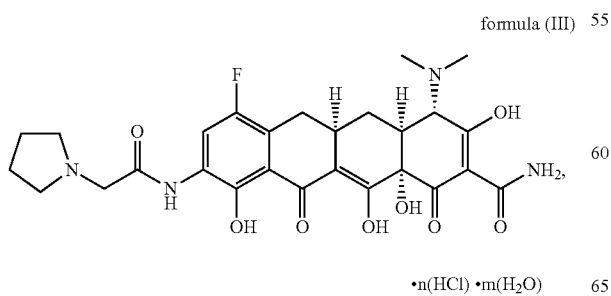

formula (III)

•n(HCl) •m(H$_2$O)

wherein n is in the range of from 1.8 to 2.2 and m is in the range of from 0.0 to 9.0
8) Crystalline eravacycline bis-hydrochloride of formula (III)

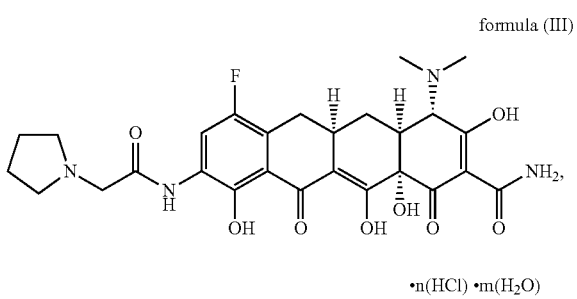 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

formula (III)

•n(HCl) •m(H$_2$O)

wherein n is in the range of from 1.9 to 2.1 and m is in the range of from 0.0 to 9.0
9) Crystalline eravacycline bis-hydrochloride of formula (III)

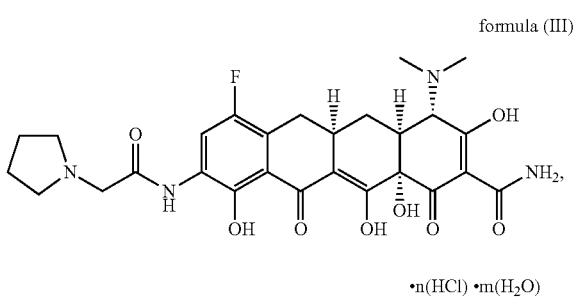 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

formula (III)

•n(HCl) •m(H$_2$O)

wherein n is 2.0 and m is in the range of from 0.0 to 9.0.
10) The crystalline eravacycline bis-hydrochloride according to any one of items 1 to 9, characterized by having a powder X-ray diffractogram comprising reflections at 2-theta angles of (5.6±0.2°) and (8.6±0.2)°, when measured with Cu-Kalpha$_{1,2}$ radiation having a wavelength of 0.15419 nm and at a temperature in the range of from 20 to 30° C.
11) The crystalline eravacycline bis-hydrochloride according to any one of items 1 to 9 characterized by having a powder X-ray diffractogram comprising reflections at 2-theta angles of (5.6±0.2)°, (6.0±0.2°) and (8.6±0.2)°, when measured with Cu-Kalpha$_{1,2}$ radiation having a wavelength of 0.15419 nm and at a temperature in the range of from 20 to 30° C.
12) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)° and (8.6±0.2)°, when measured with Cu-Kalpha$_{1,2}$ radiation having a wavelength of 0.15419 nm and at a temperature in the range of from 20 to 30° C.
13) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)°, (7.6±0.2)° and (8.6±0.2)°, when measured with Cu-Kalpha$_{1,2}$ radiation having a wavelength of 0.15419 nm and at a temperature in the range of from 20 to 30° C.

14) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)°, (7.6±0.2)°, (8.6±0.2)°, (12.1±0.2)° and (26.3±0.2)°, when measured with Cu-Kalpha$_{1,2}$ radiation having a wavelength of 0.15419 nm and at a temperature in the range of from 20 to 30° C.
15) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)°, (7.6±0.2)°, (8.6±0.2)°, (12.1±0.2)°, (26.3±0.2°) and (26.9±0.2)°, when measured with Cu-Kalpha$_{1,2}$ radiation having a wavelength of 0.15419 nm and at a temperature in the range of from 20 to 30° C.
16) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)°, (7.6±0.2)°, (8.6±0.2)°, (11.5±0.2)°, (12.1±0.2)°, (26.3±0.2°) and (26.9±0.2)°, when measured with Cu-Kalpha$_{1,2}$ radiation having a wavelength of 0.15419 nm and at a temperature in the range of from 20 to 30° C.
17) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)°, (7.6±0.2)°, (8.6±0.2)°, (11.5±0.2)°, (12.1±0.2)°, (14.3±0.2)°, (26.3±0.2°) and (26.9±0.2)°, when measured with Cu-Kalpha$_{1,2}$ radiation having a wavelength of 0.15419 nm and at a temperature in the range of from 20 to 30° C.
18) The crystalline eravacycline bis-hydrochloride according to any one of items 1 to 9 characterized by having a powder X-ray diffractogram comprising reflections at 2-theta angles of (5.6±0.2)°, (6.0±0.2)°, (7.1±0.2)°, (7.6±0.2)°, (8.6±0.2)°, (11.5±0.2)°, (12.1±0.2)°, (14.3±0.2)°, (15.2±0.2)°, (26.3±0.2°) and (26.9±0.2)°, when measured with Cu-Kalpha$_{1,2}$ radiation having a wavelength of 0.15419 nm and at a temperature in the range of from 20 to 30° C.
19) The crystalline eravacycline bis-hydrochloride according to any one of items 1 to 9 characterized by having a powder X-ray diffractogram comprising reflections at 2-theta angles of (6.0±0.2)°, (7.1±0.2)°, (7.6±0.2)°, (8.6±0.2)°, (12.1±0.2)°, (26.3±0.2)° and (26.9±0.2)°, when measured with Cu-Kalpha$_{1,2}$ radiation having a wavelength of 0.15419 nm and at a temperature in the range of from 20 to 30° C.
20) The crystalline eravacycline bis-hydrochloride according to any one of items 1 to 9 characterized by having a powder X-ray diffractogram comprising reflections at 2-theta angles of (6.0±0.2)°, (7.1±0.2)°, (7.6±0.2)°, (8.6±0.2)°, (12.1±0.2)°, and (26.3±0.2)°, when measured with Cu-Kalpha$_{1,2}$ radiation having a wavelength of 0.15419 nm and at a temperature in the range of from 20 to 30° C.
21) The crystalline eravacycline bis-hydrochloride according to any one of items 1 to 9 characterized by having a powder X-ray diffractogram comprising reflections at 2-theta angles of (6.0±0.2)°, (7.1±0.2)°, (7.6±0.2)°, (8.6±0.2)°, and (12.1±0.2)°, when measured with Cu-Kalpha$_{1,2}$ radiation having a wavelength of 0.15419 nm and at a temperature in the range of from 20 to 30° C.
22) The crystalline eravacycline bis-hydrochloride according to any one of items 1 to 9 characterized by having a powder X-ray diffractogram comprising reflections at 2-theta angles of (6.0±0.2)°, (7.1±0.2)°, (7.6±0.2)°, and (8.6±0.2)°, when measured with Cu-Kalpha$_{1,2}$ radiation having a wavelength of 0.15419 nm and at a temperature in the range of from 20 to 30° C.
23) The crystalline eravacycline bis-hydrochloride according to any one of items 1 to 9 characterized by having a powder X-ray diffractogram comprising reflections at 2-theta angles of (7.1±0.2)°, (7.6±0.2)°, (8.6±0.2)°, (12.1±0.2)°, (26.3±0.2°) and (26.9±0.2)°, when measured with Cu-Kalpha$_{1,2}$ radiation having a wavelength of 0.15419 nm and at a temperature in the range of from 20 to 30° C.
24) The crystalline eravacycline bis-hydrochloride according to any one of items 1 to 9 characterized by having a powder X-ray diffractogram comprising reflections at 2-theta angles of (7.1±0.2)°, (7.6±0.2)°, (8.6±0.2)°, (12.1±0.2)°, and (26.3±0.2)°, when measured with Cu-Kalpha$_{1,2}$ radiation having a wavelength of 0.15419 nm and at a temperature in the range of from 20 to 30° C.
25) The crystalline eravacycline bis-hydrochloride according to any one of items 1 to 9 characterized by having a powder X-ray diffractogram comprising reflections at 2-theta angles of (7.1±0.2)°, (7.6±0.2)°, (8.6±0.2°) and (12.1±0.2)°, when measured with Cu-Kalpha$_{1,2}$ radiation having a wavelength of 0.15419 nm and at a temperature in the range of from 20 to 30° C.
26) The crystalline eravacycline bis-hydrochloride according to any one of items 1 to 9 characterized by having a powder X-ray diffractogram comprising reflections at 2-theta angles of (7.1±0.2)°, (7.6±0.2°) and (8.6±0.2)°, when measured with Cu-Kalpha$_{1,2}$ radiation having a wavelength of 0.15419 nm and at a temperature in the range of from 20 to 30° C.
27) The crystalline eravacycline bis-hydrochloride according to any one of items 1 to 9 characterized by a powder X-ray diffractogram essentially the same as displayed in FIG. 1 of the present invention, when measured with Cu-Kalpha$_{1,2}$ radiation at a wavelength of 0.15419 nm and at a temperature in the range of from 20 to 30° C.
28) The crystalline eravacycline bis-hydrochloride according to any one of items 10 to 27, wherein the powder X-ray diffractogram is measured with Cu-Kalpha$_{1,2}$ radiation having a wavelength of 0.15419 nm, at a temperature in the range of from 20 to 30° C. and at a relative humidity of 30%.
29) The crystalline eravacycline bis-hydrochloride according to any one of items 1 to 28 characterized by comprising at most 20 weight % of any other physical form of eravacycline bis-hydrochloride, based on the weight of the crystalline eravacycline bis-hydrochloride.
30) The crystalline eravacycline bis-hydrochloride according to any one of items 1 to 28 comprising at most 10 weight % of any other physical form of eravacycline bis-hydrochloride, based on the weight of the crystalline eravacycline bis-hydrochloride.
31) The crystalline eravacycline bis-hydrochloride according to any one of items 1 to 28 comprising at most 5 weight % of any other physical form of eravacycline bis-hydrochloride, based on the weight of the crystalline eravacycline bis-hydrochloride.

32) The crystalline eravacycline bis-hydrochloride according to any one of items 1 to 28 comprising at most 2 weight % of any other physical form of crystalline eravacycline bis-hydrochloride, based on the weight of the crystalline eravacycline bis-hydrochloride.
33) The crystalline eravacycline bis-hydrochloride according to any one of items 1 to 28 comprising at most 1 weight % of any other physical form of eravacycline bis-hydrochloride, based on the weight of the crystalline eravacycline bis-hydrochloride.
34) The crystalline eravacycline bis-hydrochloride according to any one of items 29 to 33, wherein the other physical form of eravacycline bis-hydrochloride is amorphous eravacycline bis-hydrochloride.
35) The crystalline eravacycline bis-hydrochloride according to any one of items 1 to 34, characterized by showing a mass loss in the range of from 10.0 to 10.5 weight % based on the weight of the crystalline eravacycline bis-hydrochloride, when the crystalline eravacycline bis-hydrochloride has been equilibrated at a relative humidity in the range of from 25 to 30% and a temperature of 25° C. and when mass loss is determined by thermogravimetric analysis at a temperature in the range of from 25 to 170° C. and at a heating rate of 10 K/min.
36) The crystalline eravacycline bis-hydrochloride according to any one of items 1 to 34 characterized by showing a mass loss in the range of from 10.2 to 10.4 weight % based on the weight of the crystalline eravacycline bis-hydrochloride, when the crystalline eravacycline bis-hydrochloride has been equilibrated at a relative humidity in the range of from 25 to 30% and a temperature of 25° C. and when mass loss is then determined by thermogravimetric analysis at a temperature in the range of from 25 to 170° C. and at a heating rate of 10 K/min.
37) The crystalline eravacycline bis-hydrochloride according to any one of items 1 to 34 characterized by showing a mass loss 10.3 weight % based on the weight of the crystalline eravacycline bis-hydrochloride, when the crystalline eravacycline bis-hydrochloride has been equilibrated at a relative humidity in the range of from 25 to 30% and a temperature of 25° C. and when mass loss is then determined by thermogravimetric analysis at a temperature in the range of from 25 to 170° C. and at a heating rate of 10 K/min.
38) The crystalline eravacycline bis-hydrochloride according to any one of the preceding items characterized by having a water content in the range of from 10.0 to 10.5 weight % based on the weight of the crystalline eravacycline bis-hydrochloride, when equilibrated at a relative humidity in the range of from 25 to 30% and at a temperature of 25° C., wherein the water content is determined by Karl-Fischer-Coulometry.
39) The crystalline eravacycline bis-hydrochloride according to any one of items 1 to 27 characterized by having a water content in the range of from 10.2 to 10.4 weight % based on the weight of the crystalline eravacycline bis-hydrochloride, when equilibrated at a relative humidity in the range of from 25 to 30% and at a temperature of 25° C., wherein the water content is determined by Karl-Fischer-Coulometry.
40) The crystalline eravacycline bis-hydrochloride according to any one of items 1 to 27 characterized by having a water content of 10.3 weight % based on the weight of the crystalline eravacycline bis-hydrochloride, when equilibrated at a relative humidity in the range of from 25 to 30% and at a temperature of 25° C., wherein the water content is determined by Karl-Fischer-Coulometry.
41) The crystalline eravacycline bis-hydrochloride according to any one of the preceding items characterized by a water content in the range of from 0.0% to 20.1% when equilibrated at a relative humidity in the range of from 0 to 90% and 25.0±0.1° C., wherein the water content is determined by Karl-Fischer-Coulometry.
42) The crystalline eravacycline bis-hydrochloride according to any one of the preceding items characterized by showing a differential scanning calorimetry curve comprising an endothermic peak, which extends over a temperature range of from about 35 to 170° C., when measured at a heating rate of 10 K/min.
43) The crystalline eravacycline bis-hydrochloride according to any one of the preceding items characterized by comprising crystals having needle, lath and/or column shape.
44) The crystalline eravacycline bis-hydrochloride according to item 43, wherein the crystals have a length of not more than 30 μm.
45) The crystalline eravacycline bis-hydrochloride according to item 43, wherein the crystals have a length of not more than 20 μm.
46) The crystalline eravacycline bis-hydrochloride according to item 43, wherein the crystals have a length of not more than 10 μm.
47) A composition comprising at least 90 weight % of the crystalline eravacycline bis-hydrochloride as defined in any one of items 1 to 46 based on the total weight of the composition.
48) The composition of item 47 comprising less than 5 weight % amorphous eravacycline bis-hydrochloride based on the total weight of the composition.
49) The composition of item 47 comprising less than 2 weight % amorphous eravacycline bis-hydrochloride based on the total weight of the composition.
50) A composition comprising at least 95 weight % of the crystalline eravacycline bis-hydrochloride as defined in any one of items 1 to 46 based on the total weight of the composition.
51) The composition of item 50 comprising less than 4 weight % amorphous eravacycline bis-hydrochloride based on the total weight of the composition.
52) The composition of item 50 comprising less than 2 weight % amorphous eravacycline bis-hydrochloride based on the total weight of the composition.
53) A process for the preparation of the crystalline eravacycline bis-hydrochloride as defined in any one of items 1 to 46 comprising
   (i) providing an aqueous solution of eravacycline bis-hydrochloride in water and one organic antisolvent, wherein the aqueous solution is characterized by a water activity of at least 0.1 and
   (ii) adding crystalline eravacycline bis-hydrochloride seed crystals as defined in any one of items 1 to 46 to the solution provided in step (i);
54) The process according to item 53, wherein the eravacycline bis-hydrochloride concentration of the aqueous solution provided in step (i) is in the range of from 5 to 50 g/L.

55) The process according to item 53, wherein the eravacycline bis-hydrochloride concentration of the aqueous solution provided in step (i) is in the range of from 5 to 25 g/L.
56) The process according to item 53, wherein the eravacycline bis-hydrochloride concentration of the aqueous solution provided in step (i) is in the range of from 5 to 15 g/L.
57) The process according to any one of items 53 to 56, wherein the at least one organic antisolvent is selected from the group of ketones and ethers.
58) The process according to item 57, wherein the ketone is acetone.
59) The process according to item 57, wherein the ether is 1,2-dimethoxyethane.
60) The process according to any one of items 53 to 59, wherein the amount of seed crystals applied in step (ii) is in the range of from 1 to 10 weight %, based on the amount of eravacycline bis-hydrochloride present in the aqueous solution provided in step (i).
61) The process according to any one of items 53 to 59, wherein the amount of seed crystals applied in step (ii) is in the range of from 2 to 5 weight %, based on the amount of eravacycline bis-hydrochloride present in the aqueous solution provided in step (i).
62) The process according to any one of items 53 to 61 further comprising step (iii) adding at least one antisolvent to the suspension obtained in step (ii).
63) The process of item 62, wherein the at least one antisolvent is an organic antisolvent.
64) The process of item 63, wherein the organic antisolvent is selected from the group of ketones and ethers.
65) The process according to item 64, wherein the ketone is acetone.
66) The process according to item 64, wherein the ether is 1,2-dimethoxyethan.
67) The process according to any one of items 62 to 66, wherein the at least one antisolvent in step (iii) and the at least one organic antisolvent in step (ii) are the same.
68) The process according to any one of items 53 to 67, further comprising separating at least a part of the crystalline eravacycline bis-hydrochloride as defined in any one of items 1 to 46 from its mother liquor.
69) The process according to item 68, wherein crystalline eravacycline bis-hydrochloride is separated from its mother liquor by filtration, centrifugation, decantation or solvent evaporation.
70) The process according to item 68, wherein crystalline eravacycline bis-hydrochloride is separated from its mother liquor by filtration or centrifugation.
71) The process according to any one of items 68 to 70 further comprising washing the isolated eravacycline bis-hydrochloride crystals.
72) The process according to any one of items 53 to 71 further comprising drying the eravacycline bis-hydrochloride crystals.
73) The process according to item 72, wherein drying is performed at a temperature of 40° C. or less.
74) The process according to item 72, wherein drying is performed at a temperature of 30° C. or less.
75) The process according to item 72, wherein drying is performed at a temperature in the range of from 20 to 30° C.
76) The process according to any one of items 72 to 75, wherein drying is performed for a period in the range of from 1 to 72 hours.
77) The process according to any one of items 72 to 75, wherein drying is performed for a period in the range of from 2 to 48 hours.
78) The process according to any one of items 72 to 75, wherein drying is performed for a period in the range of from 4 to 24 hours.
79) The process according to any one of items 72 to 75, wherein drying is performed for a period in the range of from 6 to 18 hours.
80) Use of crystalline eravacycline bis-hydrochloride as defined in any one of items 1 to 46 for the preparation of a pharmaceutical composition.
81) The use according to item 70, wherein the pharmaceutical composition is intended for oral or parenteral use.
82) A pharmaceutical composition comprising an effective amount of crystalline eravacycline bis-hydrochloride according to any one of items 1 to 46, or the composition according to any one of items 47 to 52, and at least one pharmaceutically acceptable excipient.
83) The pharmaceutical composition of item 82, wherein the at least one pharmaceutically acceptable excipient is selected from the group of carriers, fillers, diluents, lubricants, sweeteners, stabilizing agents, solubilizing agents, antioxidants and preservatives, flavouring agents, binders, colorants, osmotic agents, buffers, surfactants, disintegrants, granulating agents, coating materials and combinations thereof.
84) The pharmaceutical composition of item 82 or 83 prepared by a wet processing method.
85) The pharmaceutical composition of item 82 or 83 prepared by a dry processing method.
86) The pharmaceutical composition of any one of items 82 to 85 which is an oral solid dosage form.
87) The pharmaceutical composition of item 86 which is a tablet or a capsule.
88) The pharmaceutical composition according to any one of items 82 to 87, wherein eravacycline bis-hydrochloride is present in a dose of 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 350 mg, 400 mg, 450 mg or 500 mg, calculated as eravacycline free base.
89) The pharmaceutical composition of any one of items 82 to 88, wherein the pharmaceutical composition is to be administered once daily.
90) The pharmaceutical composition of any one of items 82 to 89, wherein the pharmaceutical composition is to be administered once every second day.
91) The pharmaceutical composition of any one of items 82 to 90, wherein the pharmaceutical composition is to be administered without food.
92) Use of crystalline eravacycline bis-hydrochloride as defined in any one of items 1 to 46, or use of the composition according to any one of items 47 to 52, for the preparation of a pharmaceutical composition comprising eravacycline.
93) Use according to item 92, wherein the pharmaceutical composition comprising eravacycline is a pharmaceutical composition comprising eravacycline hydrochloride.
94) Use according to item 92 or 93, wherein the pharmaceutical composition is intended for parenteral use, in particular wherein the pharmaceutical composition is a powder for injection for infusion.

95) Use according to any one of items 92 to 94, wherein the pharmaceutical composition is a lyophilized powder for injection for infusion.
96) Process for the preparation of a pharmaceutical composition for parenteral use comprising:
   (i) providing crystalline eravacycline bis-hydrochloride as defined in any one of items 1 to 46, or the composition according to any one of items 47 to 52, and optionally at least one stabilizer selected from the group of sugars and/or sugar alcohols;
   (ii) dissolving or suspending crystalline eravacycline bis-hydrochloride and optionally the at least one stabilizer provided in step (i) in a solvent comprising water;
   (iii) adjusting the pH of the solution or suspension obtained in step (ii) by adding at least one acid or base;
   (iv) optionally filtering the solution or suspension obtained in step (iii) and
   (v) lyophilizing the solution or suspension obtained in any one of steps (ii) to (iv) to give a pharmaceutical composition comprising eravacycline.
97) Process according to item 96, wherein the sugar is lactose.
98) Process according to item 97, wherein the sugar is lactose monohydrate.
99) Process according to any one of items 96 to 98, wherein the sugar alcohol is mannitol.
100) A pharmaceutical composition obtainable or obtained by the process as defined in any one of items 96 to 99.
101) The pharmaceutical composition as defined in any one of items 82 to 91 or according to item 100 for use in the treatment and/or prevention of bacterial infections.
102) The pharmaceutical composition according to item 101, wherein the bacterial infection is caused by Gram negative bacteria.
103) The pharmaceutical composition according to item 103, wherein the bacterial infection is caused by multidrug resistant Gram negative bacteria.
104) The pharmaceutical composition according to any one of items 102 to 104, wherein the bacterial infection is selected from complicated intraabdominal and complicated urinary tract infections.

The following non-limiting examples are illustrative for preferred embodiments of the disclosure. They are not to be construed to be in any way limiting for the disclosure.

EXAMPLES

Powder X-Ray Diffraction

Powder X-ray diffraction was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40s per step (255 channels) in the angular range of 2° to 40° 2-theta at ambient conditions. A typical precision of the 2-theta values is in the range of ±0.2° 2-theta, preferably of +0.1° 2-theta. Thus, the diffraction peak of crystalline eravacycline bis-hydrochloride that appears for example at 5.6° 2-theta can appear in the range of from 5.4 to 5.8° 2-theta, preferably in the range of from 5.5 to 5.7° 2-theta on most X-ray diffractometers under standard conditions. Measurement was at room temperature and at a relative humidity of 30%.

Thermogravimetric Analysis

Thermogravimetric analysis was performed on a Mettler TGA/DSC 1 instrument. The sample (6.67 mg) was heated in a 100 microL aluminum pan closed with an aluminum lid. The lid was automatically pierced at the beginning of the measurement. The sample was heated from 25 to 200° C. at a rate of 10 K/min. Nitrogen (purge rate 50 mL/min) was used as purge gas.

Differential Scanning Calorimetry

Differential scanning calorimetry was performed on a Mettler Polymer DSC R instrument. The sample (3.02 mg) was heated in a 40 microL aluminum pan with pierced aluminum lid from 25 to 200° C. at a rate of 10 K/min. Nitrogen (purge rate 50 mL/min) was used as purge gas.

Karl-Fischer Coulometry

Water content was determined by using a Metrohm 831 KF Coulometer.

Gravimetric Moisture Sorption

Moisture sorption isotherms were recorded with an SPSx-1μ moisture sorption analyzer (proUmid, Ulm). The measurement cycle was started at ambient relative humidity (RH) of 25% and first decreased in 5% steps to 5% RH, in one step to 3% RH in a further step to 0% RH. Then RH was increased from 0% to 95% in 5% steps. The time per step was set to a minimum of 2 hours and a maximum of 6 hours. If an equilibrium condition with a constant mass of +0.01% within 1 hour was reached before the maximum time for all examined samples, the sequential humidity step was applied before the maximum time of 6 hours. If no equilibrium was achieved, the consecutive humidity step was applied after the maximum time of 6 hours. The temperature was 25±0.1° C.

At the beginning of the GMS experiment, as well as at the end of each RH-step a picture was taken of each sample in order to detect visual changes in the samples. Pictures were taken with a 2046×2046 pixel CMOS image sensor attached to a 35 mm/F 1.4 lens, which was directly connected to the cover plate of moisture sorption analyzer.

Assay Hydrochloride (Argentometric Titration)

The hydrochloride assay of eravacycline bis-hydrochloride was determined according the following procedure:

Reagents and Equipment:

| | |
|---|---|
| Water | distilled or demineralized |
| Volumetric standard substance | sodium chloride |
| Volumetric solution | 0.1M silver nitrate solution |
| Electrode | combined silver electrode, Methrom 6.0450.100 |
| Instrument | Methorom 796 titroprocessor and Methrom 685 dosimat |

Procedure

Determination of the Factor of the 0.1 M Silver Nitrate Solution:

Dissolve 40 to 60 mg of sodium chloride volumetric standard substance, weighed accurately to 0.01 mg, in approx. 50 mL of water in a titration vessel. Titrate with 0.1 M silver nitrate solution.

Test Solution

Dissolve 140 to 160 mg of eravacycline bis-hydrochloride, weighed accurately to 0.01 mg, in approximately 50 mL of water in a titration vessel and mix. Titrate with 0.1 M silver nitrate solution.

Calculation of the Factor of the Volumetric Solution:

$$\frac{m_R * C}{V_R * 58.44 * 0.1 * 100} = f$$

f=factor of the volumetric solution
$m_R$=initial mass of sodium chloride in mg
C=content of sodium chloride as in the volumetric standard substance in %
$V_R$=consumption of volumetric solution for titration of sodium chloride in mL
58.44=molecular mass of sodium chloride in g/mol
0.1=molarity of the volumetric solution
100=conversion to %
Calculation of Assay Hydrochloride (HCl) in %:

$$\frac{V_T * f * 36.46 * 0.1 * 100}{m_T} = \% \text{ hydrochloride}$$

$m_T$=initial mass of eravacycline bis-hydrochloride tested in mg
$V_T$=consumption of volumetric solution for titration of eravacycline bis-hydrochloride in mL
F=factor of the volumetric solution
36.46=molecular mass of hydrochloride in g/mol
0.1=molarity of the volumetric solution
100=conversion to %
High Performance Liquid Chromatography
Instrument: Agilent HP 1100 with Chemstation
Column: YMC-Pack Pro C18 RS; 150*4.6 mm; 3 microm
Solvent: A: 40 mmol amidosulfonic acid in water
B: 40 mmol amidosulfonic acid in water with 75% acetonitrile
Gradient:

| Time [min] | Amount A [%] | Amount B [%] |
|---|---|---|
| 0 | 90 | 10 |
| 10 | 0 | 100 |
| 15 | 0 | 100 |
| 16 | 90 | 10 |

Injection volume: 5 microL
Flow: 0.8 mL/min
Oven temperature: 40° C.
Wavelength: 254 nm Example 1: Preparation of Crystalline Eravacycline Bis-Hydrochloride Amorphous eravacycline free base, obtained according to Ronn et al. (1.00 g, 96.8 area % by HPLC) was suspended in water (15 mL). After the addition of concentrated hydrochloric acid (37% aqueous solution, 0.326 mL) a clear solution was obtained. Acetone (100 mL) was added to the solution until the solution became slightly turbid. Subsequently, the obtained milky solution was seeded with eravacycline bis-hydrochloride seed crystals (obtained according to example 2 herein) before further acetone (86 mL) was added over a period of 6 hours. The resulting suspension was stirred for 24 hours at room temperature before the solid was collected by filtration and dried at room temperature under vacuum (30 mbar) for 20 hours to obtain 0.92 g of crystalline eravacycline bis-hydrochloride.
Yield: 81% of theory; Cl-content: 9.9 weight %;
The powder X-ray diffractogram of crystalline eravacycline bis-hydrochloride obtained according to example 1 is displayed in FIG. 1. A reflection list with the corresponding relative intensities is provided in table 1. The most characteristic peaks are marked in bold print.

TABLE 1

Reflection list and relative intensities in the range of from 2.0 to 40.00; the five most characteristic reflections are marked in bold print

| Angle [±0.2 ° 2-Theta] | Relative Intensity [%] |
|---|---|
| 5.6 | 100 |
| 6.0 | 20 |
| 7.1 | 20 |
| 7.6 | 22 |
| 8.6 | 44 |
| 11.5 | 6 |
| 12.1 | 15 |
| 14.3 | 7 |
| 15.2 | 6 |
| 26.3 | 14 |
| 26.9 | 14 |

Figure 2:
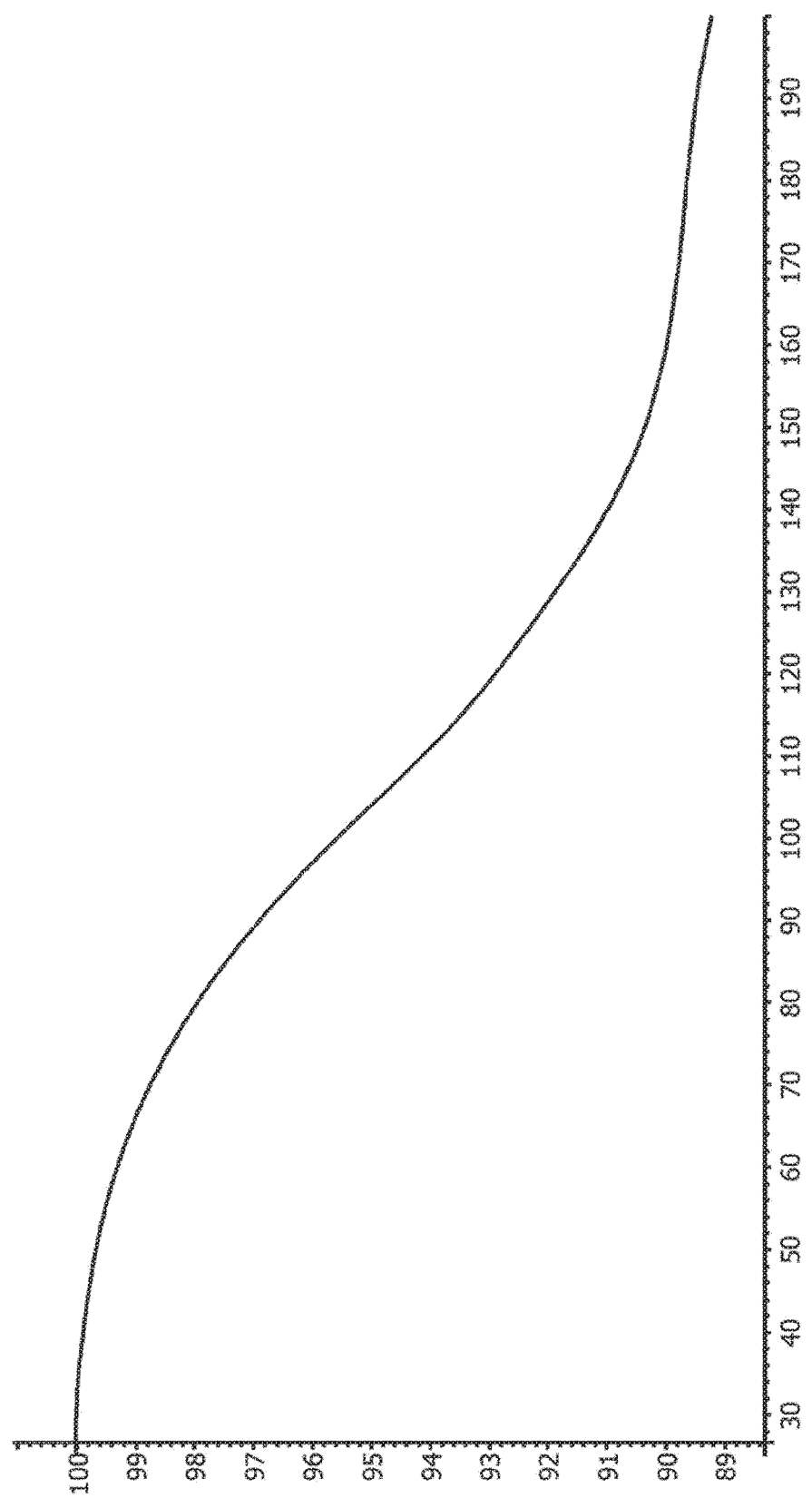
FIG. 2: illustrates a representative thermogravimetric analysis curve of crystalline eravacycline bis-hydrochloride, which was equilibrated at a relative humidity in the range of from about 25 to 30% at room temperature. The x-axis shows the temperature in degree Celsius (° C.), the y-axis shows the mass (loss) of the sample in percent (%).
Figure 3:
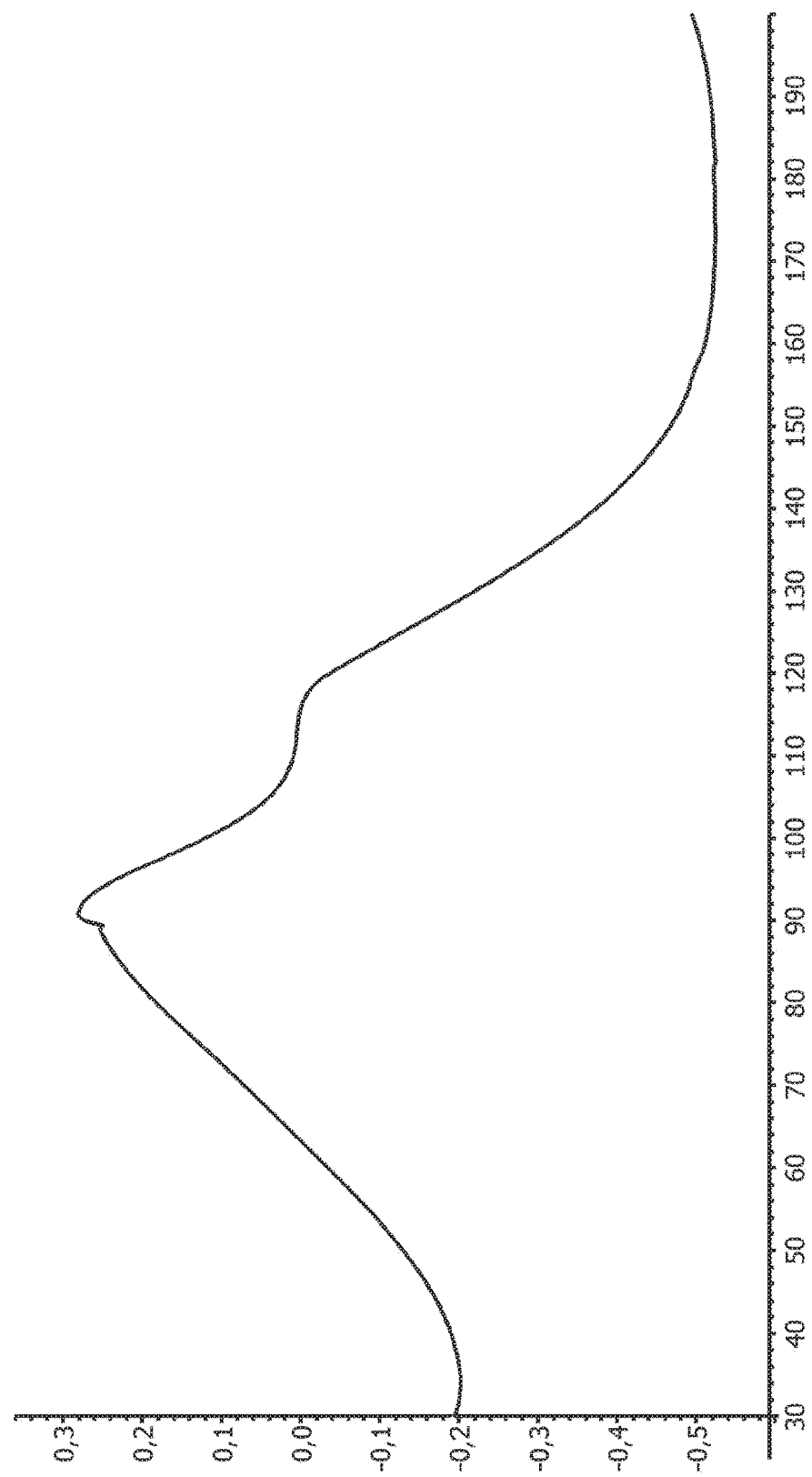
FIG. 3: illustrates a representative differential scanning calorimetric curve of crystalline eravacycline bis-hydrochloride, which was equilibrated at a relative humidity in the range of from about 25 to 30% at room temperature. The x-axis shows the temperature in degree Celsius (° C.), the y-axis shows the heat flow rate in Watt per gram (W/g) (with endothermic peaks going up).

Thermoanalytical Investigations and Water Content
The sample was equilibrated at a relative humidity of about 25 to 30% and room temperature before the thermoanalytical investigations and Karl-Fischer coulometry were conducted.
The differential scanning calorimetric curve of eravacycline bis-hydrochloride obtained according to example 1 herein shows a broad dehydration endotherm over a temperature range from about 35 to 170° C. (see also FIG. 3 herein). According to thermogravimetric analysis about 10.3 weight % (corresponding to about 4 mols of water) are lost up to a temperature of about 170° C. (see FIG. 2 herein). According to Karl-Fischer coulometry the sample had a water content of 10.3 weight %.
Gravimetric moisture sorption revealed that crystalline eravacycline bis-hydrochloride is a non-stoichiometric hydrate containing about 0 weight % of water at a relative humidity of 0% and about 20.1% of water at a relative humidity of 90%. The sample liquefied at 95% relative humidity.

Example 2: Preparation of Eravacycline Bis-Hydrochloride Seed Crystals

Step A:
A suspension of amorphous eravacycline bis-hydrochloride (25 mg, 97.2 area % by HPLC) in 1-propanol (0.5 mL) was stirred, while cycling between a temperature of 25° C. and 0° C. The suspension was first stirred at 25° C. for 1 hour, then cooled to 0° C. in 1 hour, stirred at 0° C. for 1 hour and again heated to 25° C. in 1 hour. This cycle was repeated over a period of 48 hours in total. Thereafter, the solid was isolated by centrifugation. The so obtained sample showed very weak birefringence under polarized light microscopy, which was due to the low crystallinity of the material. But it contained seed crystals of eravacycline bis-hydrochloride, which could be used to generate ever more crystalline material. This material was further used as seeds in the procedure of example 2B.
Step B:
Amorphous eravacycline bis-hydrochloride (50 mg, prepared according to Step A above) was dissolved in 0.1 M aqueous hydrochloric acid (0.25 mL). Acetone (3 mL) was added to the solution until it became slightly turbid. Subsequently, the obtained milky solution was seeded with eravacycline bis-hydrochloride crystals (obtained according to example 2A herein) and the mixture was stored in the refrigerator at a temperature of 0 to 5° C. for 120 hours. Thereafter, further acetone (6 mL) was added to the obtained suspension and stored again in the refrigerator at a temperature of 0 to 5° C. for additional 96 hours. Finally, acetone (1 mL) was added before the obtained solid was isolated by filtration, washed with acetone (1 mL) and left at room temperature for 3 hours for drying. PXRD for the first time confirmed that crystalline eravacycline bis-hydrochloride was obtained.

Reference Example 1: Preparation of Amorphous Eravacycline Bis-Hydrochloride

Figure 5:
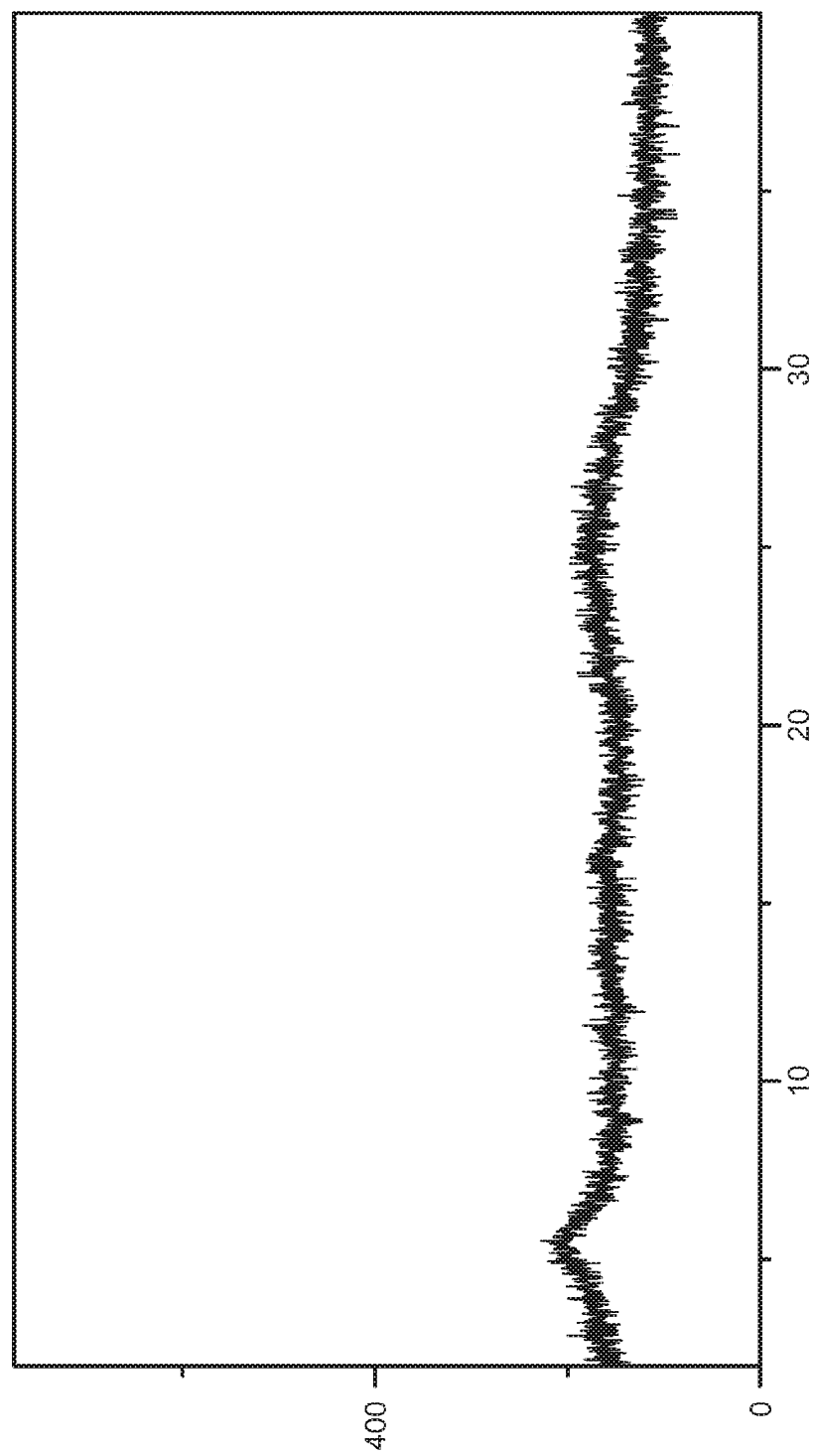
FIG. 5: illustrates the powder X-ray diffractogram of amorphous eravacycline bis-hydrochloride prepared according to comparative example 1 herein. The x-axis shows the scattering angle in ° 2-theta, the y-axis shows the intensity of the scattered X-ray beam in counts of detected photons.

A solution of amorphous eravacycline free base (2.00 g, e.g. prepared according to Ronn et. al.) in 0.1 M aqueous hydrochloride acid (80 mL) was diluted with water (80 mL) and lyophilized. The resulting fluffy and electrostically charged amorphous powder was suspended in diisopropyl ether (100 mL) for 1 hour and the solid was collected by filtration to obtain amorphous eravacycline bis-hydrochloride, which was confirmed to be amorphous by powder X-ray diffraction (see FIG. 5 herein).

Comparative Example 1: Gravimetric Moisture Sorption

Crystalline eravacycline bis-hydrochloride of the present invention and amorphous eravacycline bis-hydrochloride were both subjected to a gravimetric moisture sorption/desorption experiment using an SPSx-1μ moisture sorption analyzer (ProUmid, Ulm). The measurement cycles were started at ambient relative humidity (RH) of 20% and the RH was first decreased in 5% steps to 5% RH, in one step to 3% RH in a further step to 0% RH. Then RH was increased from 0% to 80% and decreased from 80 to 0% RH in 5% steps. Finally, the relative humidity was increased to ambient relative humidity of 20% in 3 steps of approximately 7% steps.

The time per step was set to a minimum of 2 hours and a maximum of 6 hours. If an equilibrium condition with a constant mass of 0.01% within 1 hour was reached before the maximum time for all examined samples the sequential humidity step was applied before the maximum time of 6 hours. If no equilibrium was achieved the consecutive humidity step was applied after the maximum time of 6 hours. The temperature was (25±0.1)° C.

Figure 6:
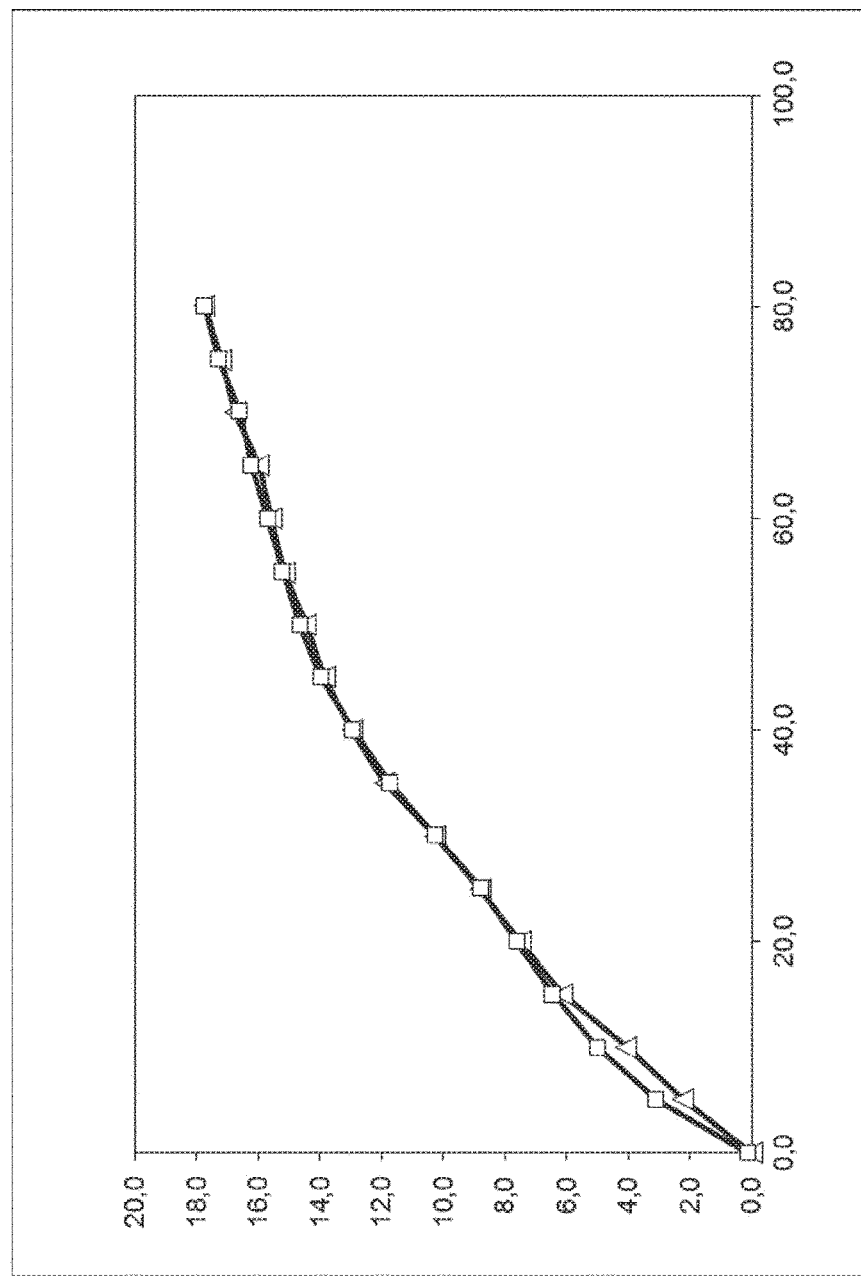
FIG. 6: illustrates representative gravimetric moisture sorption (solid line with triangles) and desorption (solid line with squares) curves of crystalline eravacycline bis-hydrochloride in the range of from 0 to 80% relative humidity. The x-axis displays the relative humidity in percent (%) measured at a temperature of $(25.0\pm0.1)°$ C., the y-axis displays the equilibrium mass change in weight percent (w-%). The sample weight at 0% relative humidity was used as reference weight.
Figure 7:
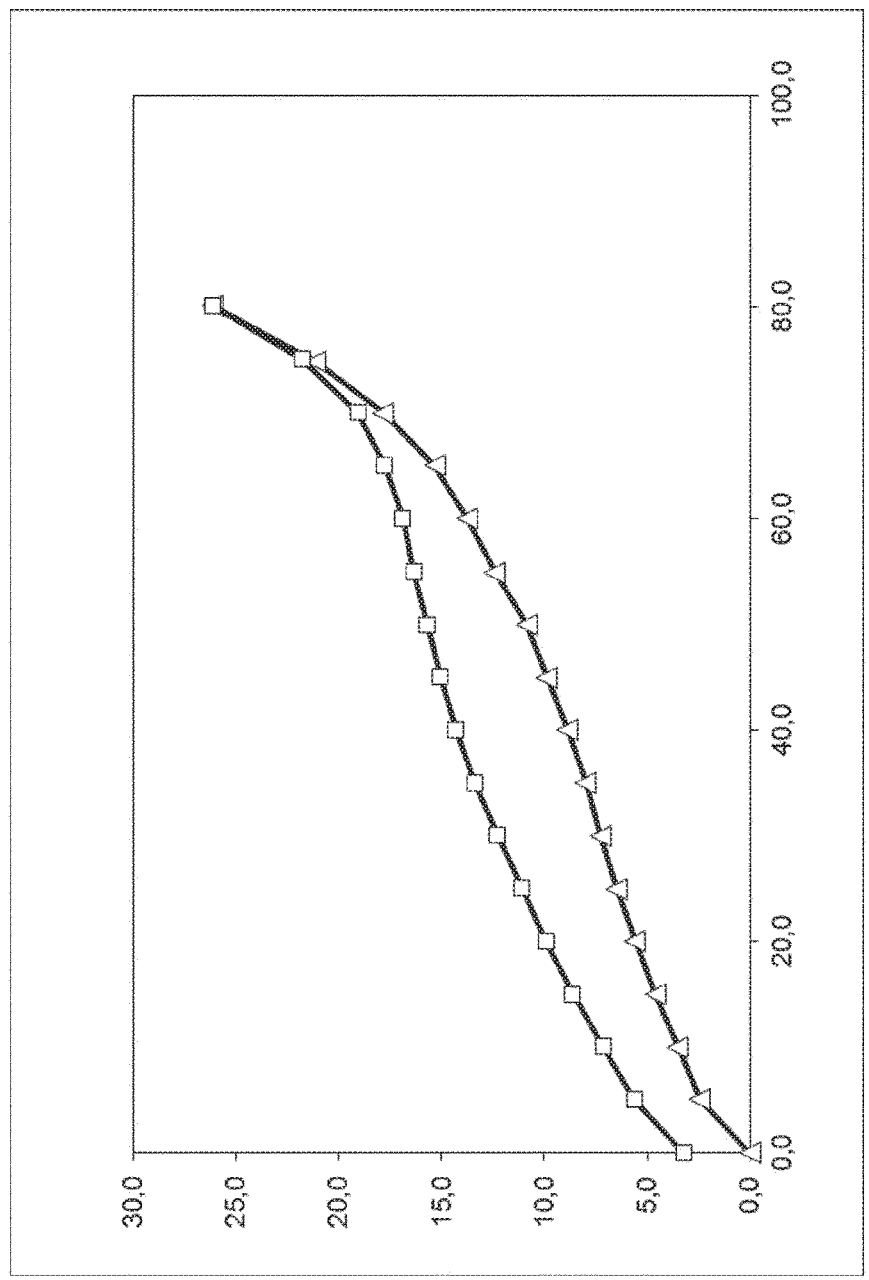
FIG. 7: illustrates representative gravimetric moisture sorption (solid line with triangles) and desorption (solid line with squares) curves of amorphous eravacycline bis-hydrochloride of the present invention in the range of from 0 to 80% relative humidity. The x-axis displays the relative humidity in percent (%) measured at a temperature of $(25.0\pm0.1)°$ C., the y-axis displays the equilibrium mass change in weight percent (w-%). The sample weight at 0% relative humidity was used as reference weight.

FIGS. 6 and 7 show the sorption and desorption cycles between 0 and 80% relative humidity respectively. As can be seen from FIG. 7, amorphous eravacycline bis-hydrochloride shows a mass increase of about 26.1 weight % during the sorption cycle from 0 to 80% RH. The hysteresis between the sorption and the desorption curve indicates that water is taken up more quickly than it is being released.

According to FIG. 6 the crystalline eravacycline bis-hydrochloride of the present invention shows a mass increase of about 17.7 weight % during the sorption cycle from 0 to 80% relative humidity. In contrast to amorphous eravacycline bis-hydrochloride, crystalline eravacycline bis-hydrochloride shows no significant hysteresis between the sorption and the desorption curve, indicating that water is taken up and released equally fast.

Comparative Example 2: Chemical Stability

Crystalline eravacycline bis-hydrochloride of the present invention and amorphous eravacycline bis-hydrochloride were subjected to accelerated stress conditions of 40° C. and 75% relative humidity. The samples were open stored in glass vials and analyzed by high performance liquid chromatography at 254 nm using the method as described in the experimental section above. The results are summarized in table 2 below:

TABLE 2

Comparison of chemical stabilities

|  | Area % crystalline eravacycline 2HCl | Area % amorphous eravacycline 2HCl |
| --- | --- | --- |
| Initial sample | 95.8 | 97.2 |
| 40° C./75% RH for 19 days | 77.1 | 31.9 |
| 40° C./75% RH for 42 days | 73.8 | 30.3 |

As can be seen from table 2, crystalline eravacycline bis-hydrochloride is chemically more stable than amorphous eravacycline bis-hydrochloride.

The invention claimed is:

1. Crystalline eravacycline bis-hydrochloride of formula (III)

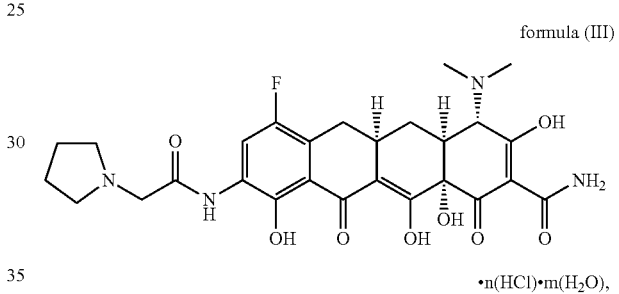

formula (III)

$\cdot n(HCl) \cdot m(H_2O)$, wherein n is in the range from 1.8 to 2.2, wherein m is in the range from about 0.0 to 9.0, and wherein the crystalline eravacycline bis-hydrochloride characterized by having a powder X-ray diffractogram comprising reflections at 2-theta angles of (5.6±0.2)°, (6.0±0.2)°, (7.1±0.2)°, (7.6±0.2)° and (8.6±0.2)°, when measured with Cu-Kalpha$_{1,2}$ radiation having a wavelength of 0.15419 nm and a temperature in the range of from 20 to 30° C.

2. The crystalline eravacycline bis-hydrochloride of claim 1, wherein the crystalline eravacycline bis-hydrochloride is a non-stoichiometric hydrate.

3. The crystalline eravacycline bis-hydrochloride according to claim 1 characterized by a water content in the range of from 8.0% to 12.5%, the crystalline eravacycline bis-hydrochloride being equilibrated at a relative humidity of 30% and 25.0±0.1° C., as determined by Karl-Fischer-Coulometry.

4. A process for the preparation of crystalline eravacycline bis-hydrochloride as defined in claim 1 comprising:
   providing an aqueous solution of eravacycline bis-hydrochloride in water and at least one organic antisolvent selected from the group consisting of ketones and ethers, wherein the aqueous solution is characterized by a water activity of at least 0.1 and,
   (ii) adding eravacycline bis-hydrochloride seed crystals to the solution provided in wherein the seed crystals are characterized by having a powder X-ray diffractogram comprising reflections at 2-theta angles of (5.6±0.2)°, (6.0±0.2)°, (7.1±0.2)°, (7.6±0.2)° and (8.6±0.2)°, when measured with Cu-Kalpha$_{1,2}$ radiation having a wavelength of 0.15419 nm and a temperature in the range of from 20 to 30° C.

5. A pharmaceutical composition comprising an effective amount of crystalline eravacycline bis-hydrochloride as defined in claim 1 and at least one pharmaceutically acceptable excipient.

6. The pharmaceutical composition of claim 5 which is an oral solid dosage form.

7. The pharmaceutical composition of claim 6 which is a tablet or a capsule.

8. Process for the preparation of a pharmaceutical composition comprising eravacycline, wherein the pharmaceutical composition is intended for parenteral use, comprising the steps of:
  providing the crystalline eravacycline bis-hydrochloride as defined in claim 1 and optionally at least one stabilizer selected from the group of sugars and/or sugar alcohols;
  (ii) dissolving or suspending crystalline eravacycline bis-hydrochloride and optionally the at least one stabilizer provided in step (i) in a solvent comprising water;
  (iii) adjusting the pH of the solution or suspension obtained in step (ii) by adding at least one acid and/or base;
  (iv) optionally filtering the solution or suspension obtained in step (iii) and
  (v) lyophilizing the solution or suspension obtained in any one of steps (ii) to (iv) to give a pharmaceutical composition comprising eravacycline.

9. A method for the treatment of bacterial infections, comprising administering an effective dosage of the pharmaceutical composition of claim 5.

* * * * *